(12) United States Patent
Fischer et al.

(10) Patent No.: US 6,895,624 B2
(45) Date of Patent: *May 24, 2005

(54) POWERED TONGUE CLEANING DEVICE

(75) Inventors: Dan E. Fischer, Sandy, UT (US); Bruce S. McLean, Sandy, UT (US)

(73) Assignee: Ultradent Products, Inc., South Jordan, UT (US)

( * ) Notice: Subject to any disclaimer, the term of this patent is extended or adjusted under 35 U.S.C. 154(b) by 264 days.

This patent is subject to a terminal disclaimer.

(21) Appl. No.: 10/094,141

(22) Filed: Mar. 7, 2002

(65) Prior Publication Data

US 2003/0167582 A1 Sep. 11, 2003

(51) Int. Cl.[7] ............................. A46B 3/02; A61B 17/24

(52) U.S. Cl. ............................. 15/22.1; 15/111; 15/160; 15/167.1; 132/308; 132/309; 132/310; 606/161

(58) Field of Search ........................... 15/22.1, 111, 160, 15/167.1; 132/308–310; 606/161

(56) References Cited

U.S. PATENT DOCUMENTS

| | | | |
|---|---|---|---|
| 585,358 A | 6/1897 | Gould | 15/188 |
| 726,727 A | 4/1903 | Mills et al. | 15/188 |
| 1,327,757 A | 1/1920 | Eggers | 15/188 |
| 1,734,429 A | 11/1929 | Hanover | 15/188 |
| 1,797,946 A | 3/1931 | Eichel | 15/188 |

(Continued)

FOREIGN PATENT DOCUMENTS

| | | |
|---|---|---|
| CH | 203802 | 6/1939 |
| CH | 333001 | 3/1959 |
| DE | 571724 | 3/1933 |
| DE | 2311043 | 9/1984 |
| GB | 2214420 | 6/1989 |

OTHER PUBLICATIONS

Product packaging for Sonicare: "The Sonic Toothbrush", *Philips Oral Healthcare, Inc.*, Copyright 2001, 5 pgs.

Owner's Booklet for Sonicare: "The Sonic Toothbrush", *Philips Oral Healthcare, Inc.*, on information and belief, available at least as early as Jan., 2002, pp. 1–10.

(Continued)

*Primary Examiner*—Mark Spisich
(74) *Attorney, Agent, or Firm*—Workman Nydegger

(57) ABSTRACT

A portable, hand-held device is employed to clean the tongue. The device includes a housing configured to be grasped by a user during a tongue cleaning procedure, a fibrous brush configured to clean tongue surfaces as the brush is moved against the surface of the tongue, and a motor assembly configured to vibrate the brush as the brush is moved against the surface of the tongue. The brush has a height that is substantially less than the width thereof, such that the configuration of the brush minimizes the elicitation of a gag reflex when the device is used to clean the tongue.

38 Claims, 17 Drawing Sheets

U.S. PATENT DOCUMENTS

| | | | |
|---|---|---|---|
| 1,861,347 A | 5/1932 | Johnson | 15/188 |
| 2,218,072 A | 10/1940 | Runnels | 15/188 |
| 2,225,331 A | 12/1940 | Campbell et al. | 15/188 |
| 2,244,699 A | 6/1941 | Hosey | 15/188 |
| 2,545,814 A | 3/1951 | Kempster | 15/188 |
| 2,783,490 A | 3/1957 | Kutik | 15/187 |
| 2,893,036 A | 7/1959 | Filler et al. | 15/176.1 |
| 2,917,057 A | 12/1959 | Busseuil | 401/129 |
| 3,007,441 A | 11/1961 | Eyer | 433/1 |
| 3,214,777 A | 11/1965 | Kutik et al. | 15/187 |
| 3,302,230 A | 2/1967 | Poppelmann | 15/167.1 |
| 3,553,759 A | 1/1971 | Kramer | 15/110 |
| 3,781,402 A | 12/1973 | Hanggi | 264/243 |
| 3,879,139 A | 4/1975 | Dahl et al. | 401/135 |
| 3,943,592 A | 3/1976 | Bhaskar et al. | 15/160 |
| D243,422 S | 2/1977 | Varga | D4/104 |
| 4,079,478 A | 3/1978 | Andrews, Sr. | 15/210.1 |
| 4,128,910 A | 12/1978 | Nakata et al. | 15/110 |
| D309,528 S | 7/1990 | Valenti | D4/104 |
| 4,958,402 A | 9/1990 | Weihrauch | 15/207.2 |
| 5,032,082 A | 7/1991 | Herrera | 433/141 |
| D332,352 S | 1/1993 | Caldwell et al. | D4/104 |
| 5,189,751 A | 3/1993 | Giuliani et al. | 15/22.1 |
| 5,226,197 A | 7/1993 | Nack et al. | 15/111 |
| 5,263,218 A | 11/1993 | Giuliani et al. | 15/22.1 |
| 5,305,492 A | 4/1994 | Giuliani et al. | 15/176.1 |
| 5,337,436 A | 8/1994 | Saxer et al. | 15/104.94 |
| 5,343,883 A | 9/1994 | Murayama | 132/322 |
| 5,378,153 A | 1/1995 | Giuliani et al. | 433/216 |
| 5,438,726 A | 8/1995 | Leite | 15/105 |
| 5,544,382 A | 8/1996 | Giuliani et al. | 15/22.1 |
| 5,613,262 A | 3/1997 | Choy-Madlonado | 15/160 |
| 5,636,988 A | 6/1997 | Murayama | 433/118 |
| RE35,712 E | 1/1998 | Murayama | 132/322 |
| D388,616 S | 1/1998 | Wieder et al. | D4/111 |
| 5,735,864 A | 4/1998 | Heisinger, Jr. | 606/161 |
| 5,749,116 A | 5/1998 | Wieder et al. | 15/160 |
| 5,766,193 A | 6/1998 | Millner | 606/161 |
| 5,796,325 A | 8/1998 | Lundell et al. | 336/233 |
| 5,800,367 A | 9/1998 | Saxer et al. | 601/164 |
| 5,815,872 A | 10/1998 | Meginniss et al. | 15/22.1 |
| D400,357 S | 11/1998 | Crosson | D4/111 |
| 5,842,247 A | 12/1998 | Decesare | 15/106 |
| D405,272 S | 2/1999 | Khalaj et al. | D4/110 |
| 5,866,116 A | 2/1999 | Yaegaki | 424/93.51 |
| 5,944,519 A | 8/1999 | Griffiths | 433/80 |
| 5,947,912 A | 9/1999 | Montagnino | 601/142 |
| 5,951,578 A | 9/1999 | Jensen | 606/161 |
| 5,967,152 A | 10/1999 | Rimkus | 132/308 |
| 5,994,855 A | 11/1999 | Lundell et al. | 318/114 |
| 6,049,934 A | 4/2000 | Discko | 15/106 |
| RE36,699 E | 5/2000 | Murayama | 433/118 |
| 6,067,684 A | 5/2000 | Kweon | 15/167.1 |
| 6,102,923 A | 8/2000 | Murayama | 606/161 |
| 6,131,228 A | 10/2000 | Chen et al. | 15/22.1 |
| 6,132,445 A | 10/2000 | Pavanelli | 606/161 |
| 6,322,573 B1 | 11/2001 | Murayama | 606/161 |

OTHER PUBLICATIONS

Philips Product Catalog, *Philips Merchandising*, Copyright 2001, pp. 1, 17, 28, and 31.

Product packaging and directions for Cybersonic ®: "Sonic Tongue Cleaning Attachment" (product removed), on information and belief, available at least as early as Dec., 2000, 2 pgs.

Photographs (taken Jun., 2002) of Cybersonic ®: "Sonic Tongue Cleaning Attachment", which, on information and belief, was available at least as early as Dec., 2000, 1 pg.

"Basic Operating Instructions", Cybersonic ®, availabile, on information and belief, at least as early as Dec., 2000.

Internet website for Sonicare, "The World's First Sonic Toothbrush for Home Use", http://www.sonicare.com, printed on Mar. 7, 2002, Copyright 2000 and 2001, pp. 1–19.

Internet advertisement, "Bad Breath Never Again!". http://www.cleanbreath.com/1free_sample.html, Copyright 1997–2000, OraSweet Corporation, printed on Mar. 7, 2002, pp. 1–4.

Internet advertisement, "TimeMachine Electric Toothbrush for Kid's", http://www.just4teech.com/product/Oralgiene/timemachine.html, Copyright 1997–2001, revised Feb. 24, 2002, printed on Feb. 27, 2002, pp. 1–2.

Internet advertisement, Electric Toothbrush, Irrigators, and more at Just4teeth.com, http://www.just4teech.com/electric.html, Copyright 1997–2001, revised Feb. 24, 2002, printed on Feb. 27, 2002, pp. 1–4.

Internet advertisement, "Electric Toothbrush LOW prices!", http://www.just4teech.com/?source:Overture, Copyright 1997–2001, printed on Feb. 27, 2002, pp. 1–2.

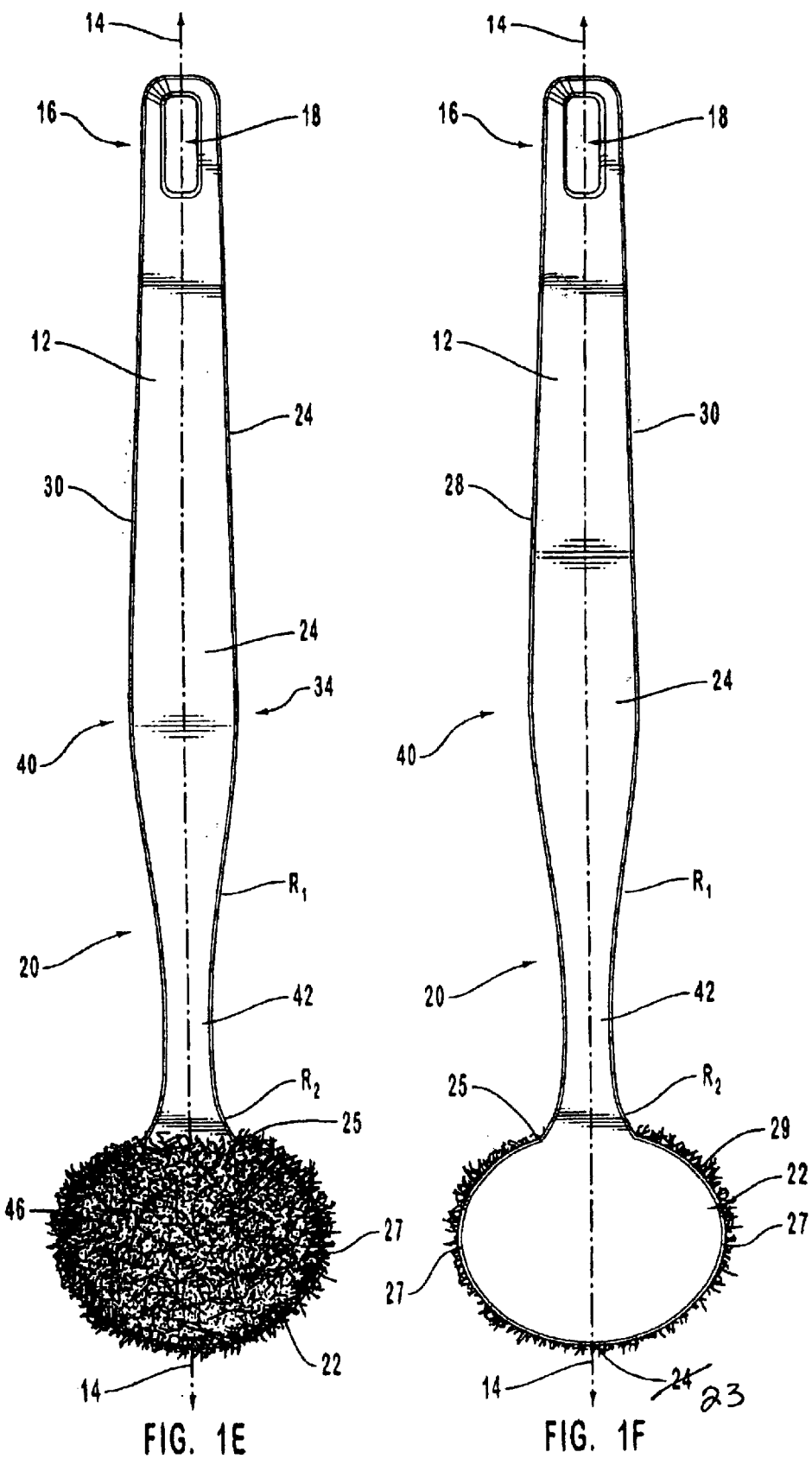

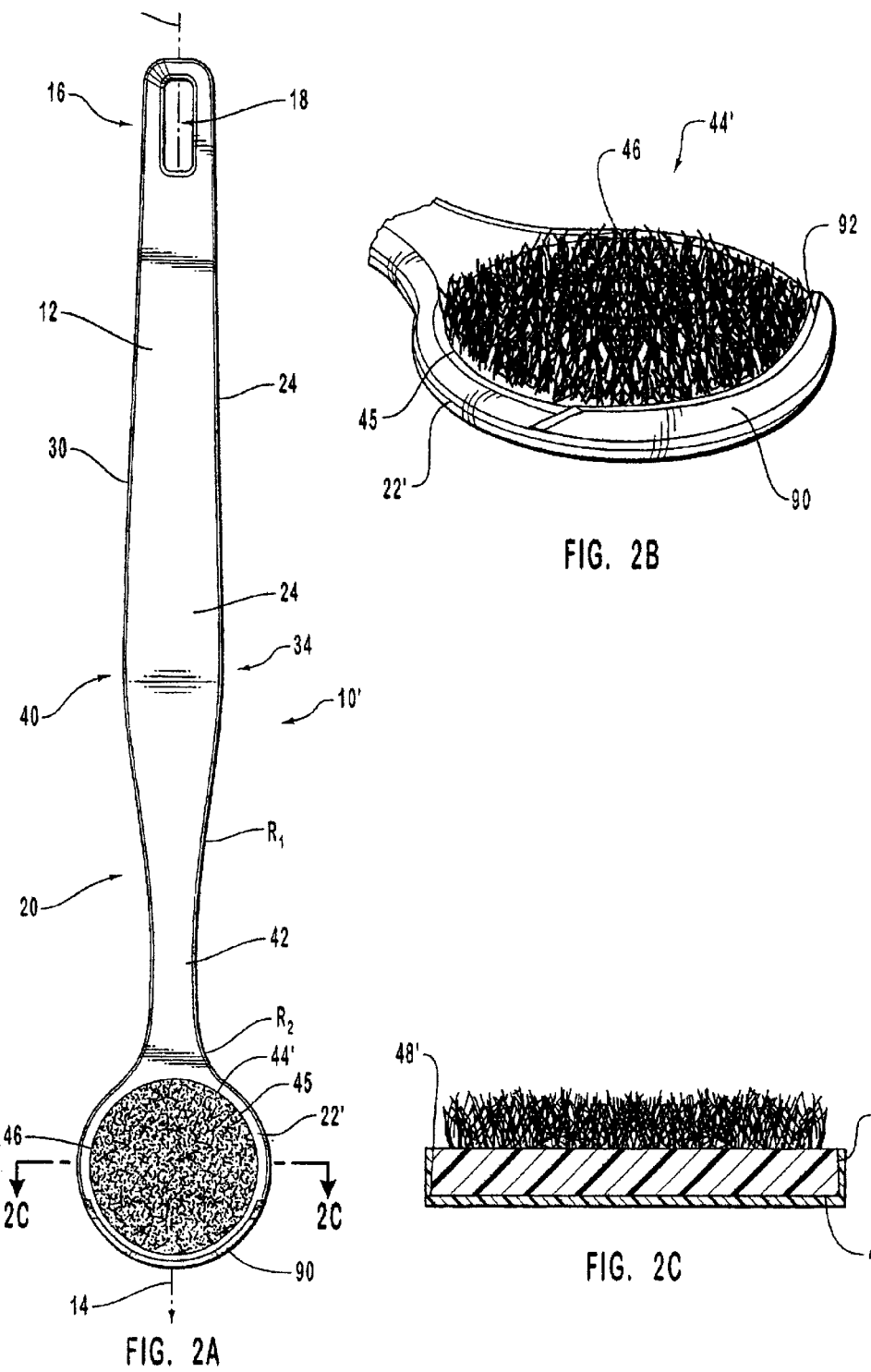

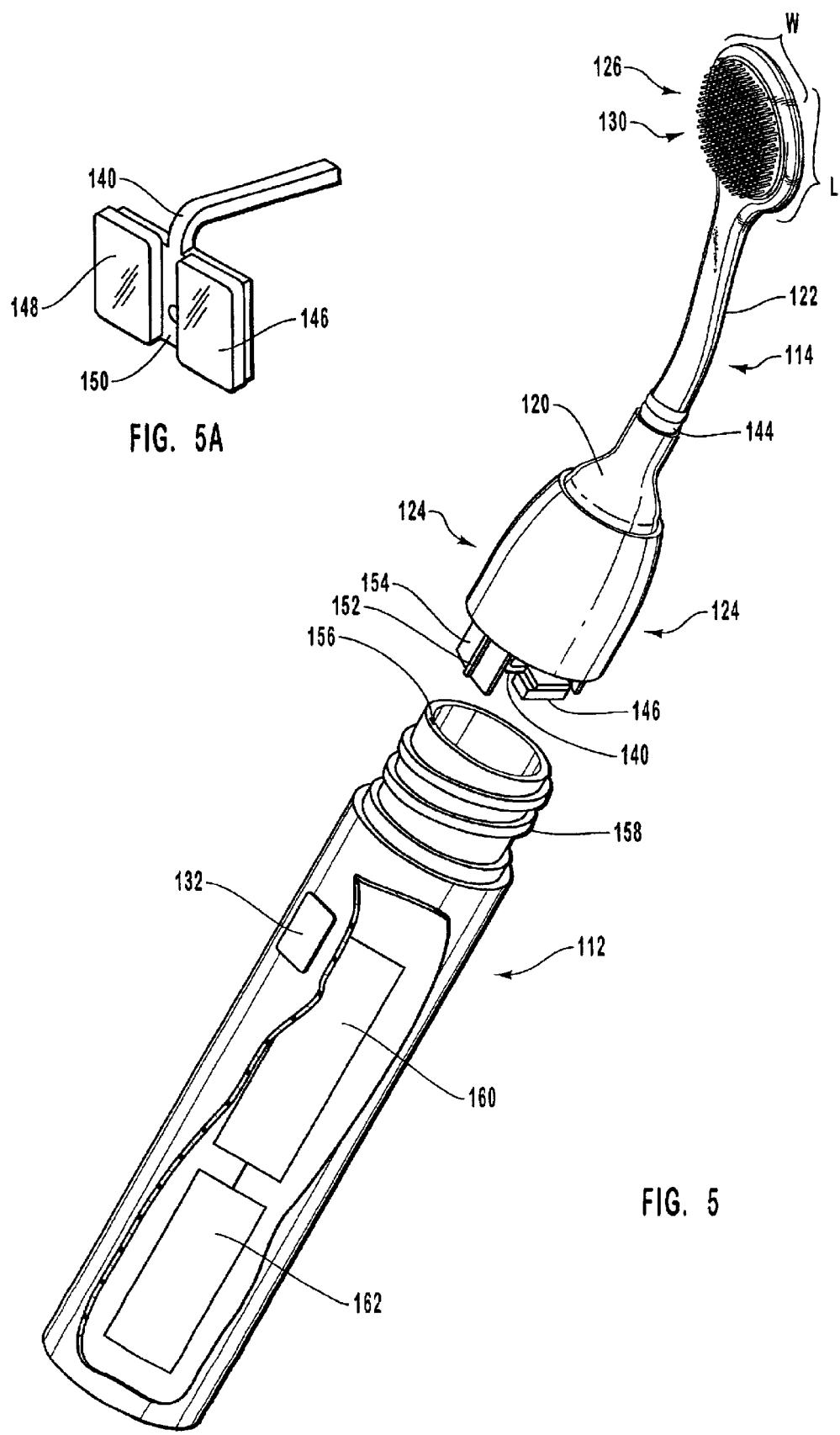

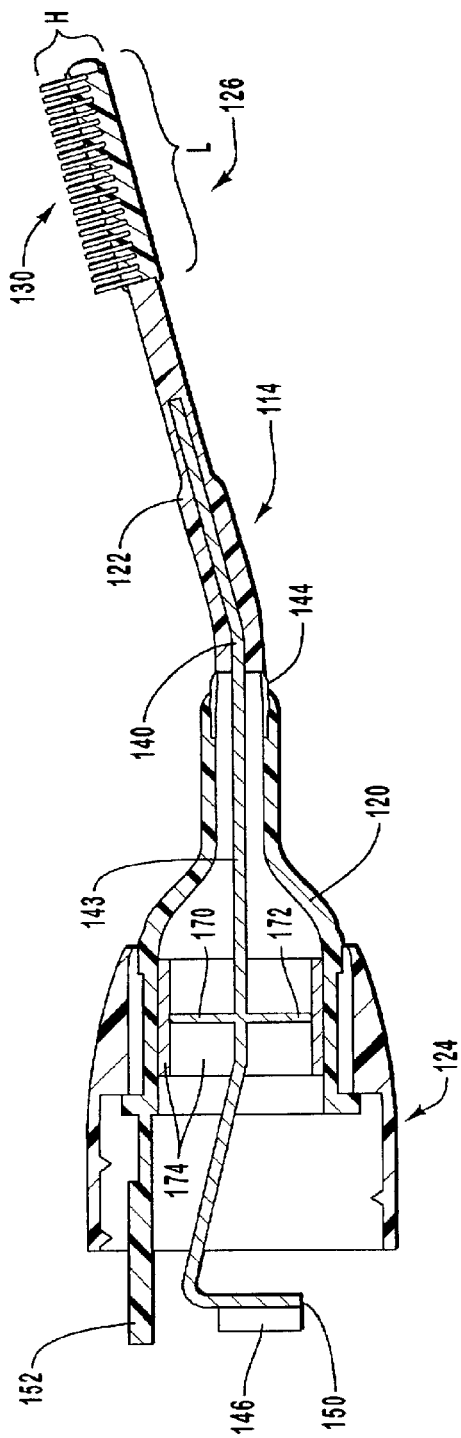
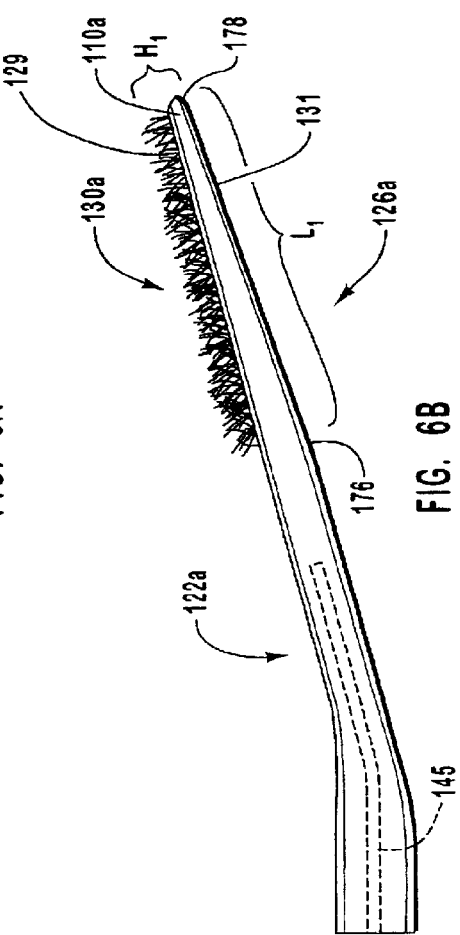
FIG. 6A
FIG. 6B

POWERED TONGUE CLEANING DEVICE

BACKGROUND OF THE INVENTION

1. The Field of the Invention

The present invention generally relates to an oral hygiene device and, in particular, to a tongue cleaning device that provides for convenient and effective cleaning of the tongue, without causing the user to gag or choke.

2. Description of Related Art

Proper care of a person's mouth or oral cavity is very important for good oral hygiene. Generally, individuals who desire good oral hygiene brush and floss their teeth on a consistent basis, but they frequently neglect to clean their tongue. The tongue is important to clean because bacteria, food and other foreign matter can buildup on the dorsum or upper surface of the tongue. In order to have good oral hygiene, these materials need to be carefully removed from the outer surface of the tongue.

The tongue, however, is not easy to clean because it is an irregularly shaped, mobile mass of striated muscles that can rapidly change its shape and configuration. Additionally, the tongue is difficult to clean because it has a rough, nonuniform outer surface and it is covered with mucous membrane. In greater detail, the tongue includes a front or anterior portion that constitutes about two-thirds of the body of the tongue. This front portion of the tongue, which includes the apex or tip, is generally positioned horizontally in the mouth and it is thickly covered with various types of papillae. The papillae project outwardly from the upper surface of the tongue to create the roughened surface. The rear or posterior portion of the tongue, located near the throat, typically has a more nodular or bossed surface and it is covered with numerous muciparous glands and lymph follicles. The tongue also includes about 5,000 to 10,000 taste buds that are scattered over the upper and side surfaces of the tongue. These different structures and surfaces create numerous mounds, ridges, peaks, protrusions, furrows, grooves and folds of various shapes and sizes. This lack of evenness makes cleaning the tongue very difficult because food particles and other debris often become trapped or encrusted in these various nonuniform surfaces.

It is known to use conventional toothbrushes to clean the tongue. The long bristles of conventional toothbrushes, however, are designed to clean the hard outer surfaces of the teeth and the long bristles are pliable to minimize abrasiveness to the enamel surfaces of the teeth. The long bristles of conventional toothbrushes are also designed to create toothpaste lather, contact the gums, reach below the gingival tissue and not damage the teeth or surrounding gingival tissue. Additionally, the long bristles allow the toothbrush to reach into the crevices between and around teeth, while providing a safe margin between the tips of the bristles and the hard plastic base of the toothbrush. Further, conventional toothbrushes often have an elongated head with a narrow width to fit into the constricted areas of the mouth, such as between the teeth and the cheek. Accordingly, conventional toothbrushes have a narrow width and a high profile measured from the tips of the bristles to the outer surface of the head of the toothbrush.

The long bristles of conventional toothbrushes, however, are not suitable to reach and clean the bottom surfaces of the various folds, grooves and ridges in the tongue because the bristles are not sufficiently rigid. Additionally, the long bristles and relatively thick body of the toothbrush often touch the pharynx, soft palate or posterior portion of the mouth and this frequently elicits a "gagging" or "choking" response by the user. Further, while the generally slender configuration of a conventional toothbrush allows it to fit into the narrow spaces between teeth and cheek, it prevents the toothbrush from quickly or efficiently cleaning the tongue because of its small contact area. Accordingly, conventional toothbrushes are generally unsuitable for cleaning the tongue.

In response to the need for brushes and other devices specifically designed for cleaning the tongue, various designs have been developed as disclosed in U.S. Pat. No. 5,951,578 issued to Jensen, U.S. Pat. No. 5,944,519 issued to Griffiths, U.S. Pat. No. 5,842,247 issued to Decesare, U.S. Pat. No. 5,735,864 issued to Heisinger, Jr., U.S. Pat. No. 5,749,116 issued to Wieder et al., U.S. Pat. No. 5,735,864 issued to Heisinger, Jr., U.S. Pat. No. 5,613,262 issued to Choy-Maldonado, U.S. Pat. No. 4,079,478 issued to Andrews, U.S. Pat. No. 3,943,592 issued to Bhaskar et al., U.S. Design Pat. No. 243,422 issued to Varga, U.S. Design Pat. No. 405,272 issued to Khalaj et al., U.S. Design Pat. No. 400,357 issued to Crosson, U.S. Design Pat. No. 388,616 issued to Wieder et al., U.S. Design Pat. No. 332,352 issued to Caldwell et al., U.S. Design Pat. No. 309,528 issued to Valenti, and U.S. Design Pat. No. 243,422 issued to Varga.

One design approach described in several of these patents is to use the same type of clusters of bristles used with conventional toothbrushes which have been shortened to minimize the occurrence of the gag reflex. Such fibers are typically made from nylon. Examples of such designs are disclosed in U.S. Pat. No. 5,842,247 issued to Decesare U.S. Pat. No. 5,749,116 issued to Wieder et al., U.S. Pat. No. 5,613,262 issued to Choy-Maldonado, U.S. Design Pat. No. 332,352 issued to Caldwell et al., U.S. Design Pat. No. 309,528 issued to Valenti, and U.S. Design Pat. No. 243,422 issued to Varga.

There are several problems with such brushes that utilize clusters of fibrous bristles. Since the bristles are typically made of nylon, the shortness of the bristles tends to result in insufficient flexibility. More particularly, the short bristles are too stiff and are resultingly incapable of adequately conforming to the varied surface features and contours of the tongue to optimally clean the tongue. Additionally, since the rigidity increases as the length is decreased, the length cannot be sufficiently reduced to result in a desirable vertical profile. The vertical profile includes the combined height of the bristles and the head from which the bristles extend.

As indicated above, it is desirable to reduce the vertical profile as much as possible in order to minimize the likelihood of inducing a gag reflex. The tongue brush sold by Enfresh Products LLC is an example of a tongue brush with a reduced vertical profile. These brushes have a head with clusters of fiber bristles extending from the head. Note that the brushes sold by Enfresh Products LLC are marked with Design Pat. No. 400,357 which issued to Crosson. In addition to Design Pat. No. 400,357, these tongue brushes can be viewed at www.enfresh.com. The tongue brushes marked with Design Pat. No. 400,357 have a vertical profile of about 0.4 inch or 10.16 mm. Note that the clusters of fibrous bristles of the tongue brushes, which are marked with Design Pat. No. 400,357, have a length of about 0.2 inch or 5.8 mm and are very stiff. The bristles in the brush sold by Enfresh Product LLC are relatively stiff as they are made from the same material as toothbrush bristles but are much shorter. More particularly, the bristles have a length to thickness ratio of about 40:1 while toothbrush bristles have a length to thickness ratio of about 75:1.

Another tongue brush having clusters of bristles has an even smaller vertical profile. U.S. Pat. No. 5,951,578 issued to Jensen indicates at column 4, lines 36–41 that the preferred vertical profile of the brush disclosed therein is approximately 5/16 inch (0.3125 inch and 7.9375 mm) based on the combined thickness of the forward end 36 of the brush and the associated bristles.

One approach to achieving a reduction in the vertical profile is disclosed in U.S. Pat. No. 3,943,592 issued to Bhaskar et al. Bhaskar et al. utilizes a laminate of Velcro® tape adhered onto an elongated member. As indicated at column 6, line 21 in Bhaskar et al., the resulting combined vertical profile of the tape on the elongated member is 3 mm. Bhaskar et al. indicates that this lower profile provides a significant advantage over the use of toothbrushes, which have a vertical profile of 15 mm. However, the structure used to achieve this low profile is not easily cleaned for repeated use. More particularly, the hooks of the Velcro® tape are not easily cleaned. Additionally, adhesion of the other adhesive side of the tape to wood may lead to bacterial growth that is difficult to eliminate. Accordingly, a tongue brush having a head with two parts including a laminate brush portion adhered onto a head such as that disclosed in U.S. Pat. No. 3,943,592 may not be useable in a repeated manner due to the difficulty involved in cleaning it. U.S. Pat. No. 4,079,478 issued to Andrews is another laminate that presents similar difficulties in maintaining the brush in a clean condition for repeated use. Obviously retention of residual bacteria diminishes the ability of such brushes to effectively clean.

A tongue brush having clusters of fibrous bristles, such as those discussed above, can also be difficult to maintain in a clean condition. More particularly, since the bristles are held very tightly together, particularly at the base of the cluster, the cluster may not be fully clean when used again. Further, since the bristles extend into the head some portions may even be impossible to fully clean.

Another approach to tongue cleaning is disclosed in U.S. Pat. No. 5,944,519 which issued to Griffiths. The cleaner has a compressible foam pad that has been folded onto a handle. The compressible pad is covered with fibers that have been flocked onto its surface so that the entire surface of the compressible pad can be used to clean the tongue. The compressible pad is a porous foam so that it can hold mouthwash. However, a disadvantage resulting from the porosity of the foam is that it may be difficult to adequately clean it. Another disadvantage is that the manner in which the pad is adhered to the handle causes it to have a large vertical profile.

Further, various mechanical devices to clean a person's tongue are also known. These devices are generally complex mechanical systems that agitate the bristles of the brush. These complex devices, however, are expensive, prone to breaking and difficult to control.

SUMMARY OF THE INVENTION

A need therefore exists for a tongue cleaning device that provides convenient and effective cleansing of the tongue, and eliminates the above-described disadvantages and problems.

One aspect of the present invention is a tongue cleaning device that can remove food, debris, bacteria, plaque and other matter from the plurality of grooves, furrows and folds in the outer surface of the tongue. The tongue cleaning device includes an elongated body with a handle and a cleansing head. The handle is ergonomically designed to allow the user to hold the tongue cleaning device comfortably and in proper alignment with the outer surface of the tongue.

The cleansing head includes a brush portion with a plurality of flocked fibers adhered onto the brush portion by an adhesive. The tongue cleaning device may also include a scraper to assist in scraping away food and other foreign matter from the tongue. It will be appreciated that while the tongue cleaning device can be used with a cleanser, use of the cleanser is not required.

The brush portion is preferably an integral portion of the head. The brush portion may also be molded into an aperture in the head as part of a two-part molding process such that the brush portion and the head are sealed together. The brush portion may also be separately formed as a brush insert that is inserted into an aperture in the head.

As indicated above, the fibers of the cleansing head, more particularly the brush portion, are flocked onto the brush portion. The fibers allow the tongue cleaning device to cleanse the tongue by dislodging bacteria, food and other matter from the outer surface of the tongue. Advantageously, the fibers allow intense scrubbing of the deeper furrows, folds and grooves on the upper surface of the tongue. Additionally, the tongue cleaning device can clean both the macroscopic and microscopic portions of the tongue effectively.

A significant advantage of the use of flocked fibers is the resulting vertical profile of the cleansing head and fibers, thereby minimizing the potential for eliciting a gag reflex when cleaning the tongue. In particular, the cleansing head has a relatively small thickness and the fibers have a relatively short length such that the overall profile of the cleansing head is relatively thin. This allows the cleansing head to clean the posterior portion of the tongue without touching the pharynx, soft palate or posterior portion of the mouth and causing a gag reflex.

The present invention is advantageously simple to manufacture and it requires little or no assembly. Thus, the manufacturing costs are relatively inexpensive. Additionally, the tongue cleaning device can be readily cleaned and reused, or it can be readily disposed. The tongue cleaning device may also include a replaceable brush portion that allows the brush portion to be replaced, or a brush portion with a different type or fibers to be used.

Another aspect of the present invention relates to a powered tongue brush that can be used to conveniently clean the tongue of a user without requiring the user to perform the scrubbing action that is required with a manual brush. Employing the powered tongue brush, a user can place a brush head of the device into the user's mouth, then allow it to move against the tongue on a first location. The user can then reorient the brush head into a new position once sufficient scrubbing has been achieved in the first location. The powered, portable, hand-held tongue cleaning device comprising a hand-held housing, a brush head movably coupled to the housing, and a motor assembly in the hand-held housing that moves the brush head as the user holds the handle of the device. The powered tongue cleaning device thereby serves as a convenient device for cleaning the tongue.

Another aspect of the invention relates to an improved scraper that allows side to side or front to back cleaning.

Further aspects, features and advantages of the present invention will become apparent from the detailed description of the preferred embodiments that follows.

BRIEF DESCRIPTION OF THE DRAWINGS

The appended drawings contain figures of preferred embodiments of the present tongue cleaning device. The above-mentioned features of the tongue cleaning device, as well as other features, will be described in connection with the preferred embodiments. The illustrated embodiments, however, are only intended to illustrate the invention and not limit the invention. The drawings contain the following figures:

FIG. 1E is a top view of the tongue cleaning device shown in FIG. 1A;

FIG. 1F is a bottom view of the tongue cleaning device shown in FIG. 1A;

FIG. 2A is a top view of another embodiment of the tongue cleaning device having a brush portion molded into the head;

FIG. 2B is an enlarged partial perspective view of the tongue cleaning device shown in FIG. 2A, illustrating the cleansing head;

FIG. 2C is a cross-sectional view of the tongue cleaning device shown in FIG. 2A;

FIG. 5 is an exploded view of the powered tongue cleaning device of FIG. 4.

FIG. 5A is a view of first and second magnets coupled to a rear plate of a lever partially shown in FIG. 5.

FIG. 6A is a cross sectional view of a tip and neck of the device of FIG. 4.

FIG. 6B demonstrates an alternate brush head and arm that may be mounted on the device of FIG. 6A.

DETAILED DESCRIPTION OF THE PREFERRED EMBODIMENTS

The present invention is generally directed towards a tongue cleaning device that provides convenient and effective cleansing of the tongue. The principles of the present invention, however, are not limited to tongue cleaning devices. It will be understood that, in light of the present disclosure, the tongue cleaning device disclosed herein can be successfully used in connection with other types of oral hygiene devices.

Additionally, to assist in the description of the tongue cleaning device, words such as top, bottom, front, rear, right and left are used to describe the accompanying figures. It will be appreciated, however, that the present invention can be used in a variety of desired positions—including various angles, sideways and even upside down.

A detailed description of the tongue cleaning device now follows. Note that, the main components of the tongue cleaning device including the handle 12 and the head 22 are described and then the unique features of the brush portion 44 and its flocked fibers 46 are described in detail.

Figure 1A:
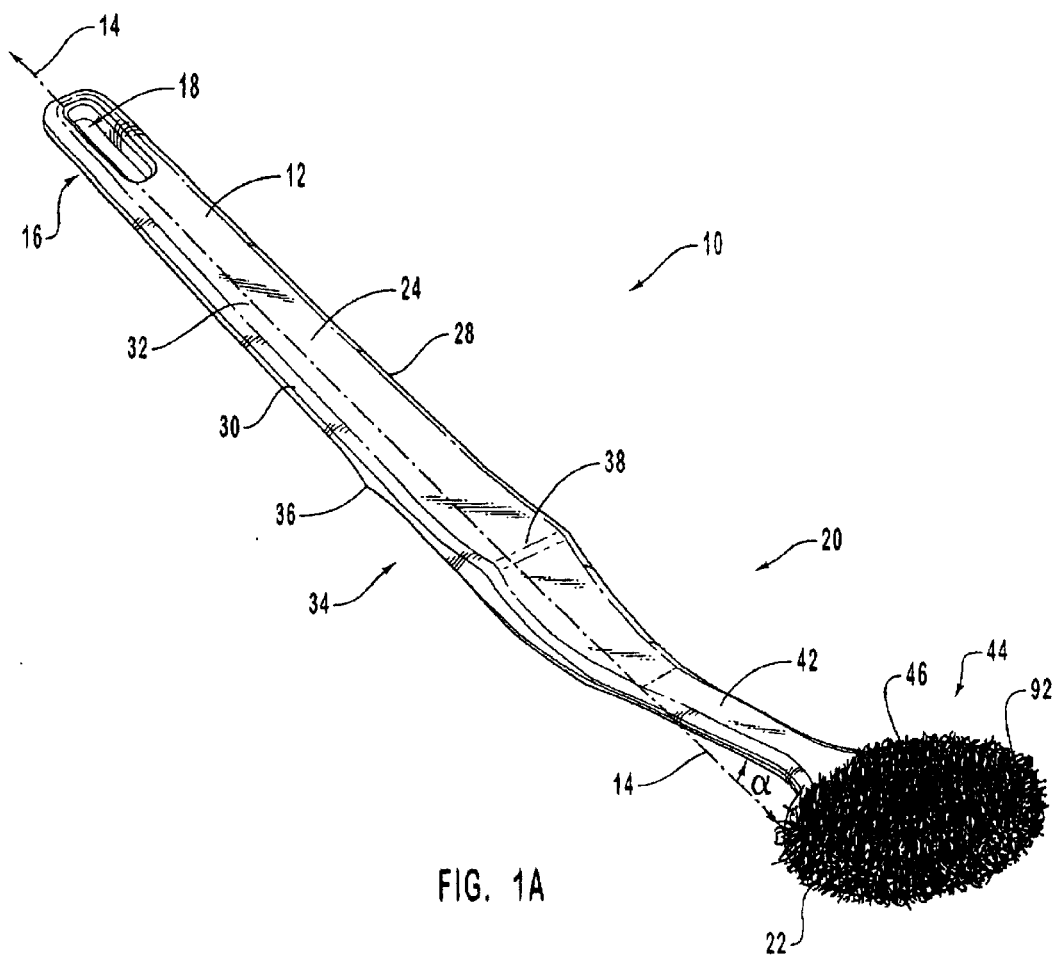
FIG. 1A is a perspective view of a tongue cleaning device in accordance with a preferred embodiment of the present invention.
Figure 1B:
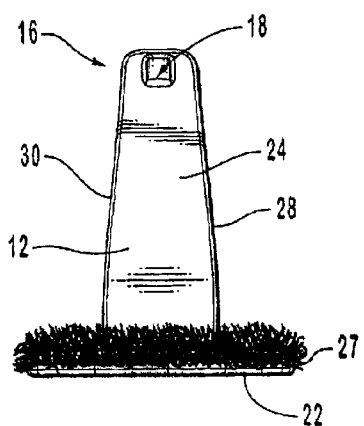
FIG. 1B is a front view of the tongue cleaning device shown in FIG. 1A.

As seen in FIG. 1A, the tongue cleaning device 10 includes an elongated handle 12 that extends generally along a longitudinal axis 14. The handle 12 includes a first end 16 with an aperture 18 that allows the tongue cleaning device 10 to be hung or supported, and a second end 20 with a cleansing head 22. The cleansing head 22 is integrally attached to the handle 12 to form a one-piece tongue cleaning device 10, but the head can also be removably or permanently attached to the handle. The handle 12 has a generally rectangular cross-section with an upper surface 24, a lower surface 26 (FIG. 1C), a right side 28 and a left side 30. The ends, surfaces and sides of the tongue cleaning device 10 are rounded or curved for comfort and safety.

The elongated handle 12 is constructed of a generally rigid material such as plastic. In particular, the handle 12 may be constructed from various materials including synthetic materials and polymers such as polyethylene, polypropylene, vinyl or nylon. The handle 12 has a length between about 5 inches to about 7 inches measured from the first end 16 to the second end 20, for example, a width of about 0.5 inch and a thickness of about 0.125 inch, for example, but the handle can have any suitable size or dimensions depending upon, for example, the type of materials used to construct the handle or the intended use of the tongue cleaning device 10. For instance, the handle 12 could be larger if the tongue cleaning device 10 is intended to be used by adults, or smaller if it is intended to be used by children.

Advantageously, the handle 12 is ergonomically designed to allow the user to comfortably hold the tongue cleaning device 10. Specifically, the handle 12 includes a generally straight body portion 32 in which the upper surface 24 is generally parallel to the lower surface 26. The handle 12 also includes gripping portions 34 with one or more curved surfaces to allow the user to easily hold the tongue cleaning device 10. The gripping portions 34 include a first arcuate portion 36 located on the lower surface 26 and a second arcuate portion 38 located on the upper surface 24 of the handle 12. These arcuate portions 36 and 38 are designed to provide an engagement fit with the fingers and thumb of the user, respectively, and prevent the handle 12 from slipping during use of the tongue cleaning device 10. Additionally, the handle 12 may include gripping portions that are textured, have nonslip surfaces or include various types of outwardly extending projections that allow the user to securely grip the tongue cleaning device 10. These various gripping portions may be especially beneficial if the handle is wet or being cleaned.

The handle 12 and the gripping portions 34 aid in properly positioning the tongue cleaning device 10 relative to the tongue. Specifically, the handle 12 and gripping portions 34 help position cleansing head 22 generally parallel to the outer surface of the tongue. In contrast, the handle of a conventional toothbrush is often designed to position the toothbrush head at an angle relative to the user's teeth. Additionally, the handle 12 and gripping portions 34 of the tongue cleaning device 10 are equally effective for right and left handed users.

As best seen in FIG. 1E and FIG. 1F, the right side 28 and the left side 30 of the handle 12 are tapered. Preferably, the sides 28 and 30 are tapered in a generally linear manner from a central portion 40, located proximate the gripping portions 34, towards the first end 16 of the handle 12. In one embodiment, the central portion 40 has a width of about 0.6 inch and the first end has a width of about 0.4 inch. The sides 28 and 30 are also tapered from the central portion 40 towards a neck 42 located between the cleansing head 22 and the handle 12. The narrowed neck 42 allows the cleansing head 22 to be easily inserted and moved within the user's mouth. The neck 42 is preferably smoothly tapered at a first radius of curvature $R_1$ from the central portion 40 to the neck 42 and at a second radius of curvature $R_2$ from the neck 42 to the cleaning head 22. It will be appreciated, however, that the cleansing head 22 can be connected to the handle 12 in any desired manner and the handle 12 can have any suitable shape and configuration. The transition from neck 42 to cleansing head 22 is considered to be an end of handle 12.

The general shape and configuration of handle 12 enables tongue cleaning device 10 to be stored in a similar manner and location as a conventional toothbrush. Additionally, the tongue cleaning device 10 can be hygienically cleaned by rinsing it. It will be appreciated, however, that the tongue cleaning device 10 can be cleaned and stored in any suitable manner. Alternatively, the tongue cleaning device 10 can be disposed of after use. Handle 12 is an example of handle means for enabling a user to grasp one end of the tongue cleaning device as the opposite end is directed by the user to facilitate a cleaning procedure in the user's mouth.

As best seen in FIG. 1E and FIG. 1F, cleansing head 22 has a curved shape with elongated opposing lateral ends 27. More particularly, cleansing head 22 is oblong or elliptical as its lateral ends 27 extend outward such that the distance between its lateral ends 27 is greater than the distance from its top 23 to its base 25 which transitions to neck 42. Other cleansing heads are shown that are generally circular at 22' and 22" respectively in FIG. 2A and FIG. 3A. It will be appreciated, however, that the cleansing head 22 can have any suitable size or shape such as oval, elongated, circular or rectangular. If the cleansing head is noncircular, it preferably has smooth, rounded corners to prevent abrasion and irritation of the mouth.

In one embodiment, the outside diameter of a cleansing head having a circular configuration is about 1.125 inch, for example, so that the head fits comfortably within the user's mouth and to maximize the cleaning area. While the cleansing head 22 may have an outside diameter that is larger than about 1.125 inch for adults, the diameter may be about 1.0 inches or smaller for children. As best seen in FIG. 1A and FIG. 1D, neck 42 is at an angle relative to straight body portion 32. Since cleansing head 22 extends from neck 42, the angle of neck 42 relative to straight body portion 32 determines the angle between cleansing head 22 and handle 12. The angle, identified in the FIG. 1A and FIG. 1D as α, between cleansing head 22 and handle 12 is of about 20°. An angle α of about 20° facilitates cleaning of the tongue, but the angle can be larger or smaller, depending, for example, upon the configuration of the handle 12 or intended use of the tongue cleaning device 10. Such an angle enhances the ability to pull fibers 46 across the tongue while also pushing downward. More particularly, the angle provides increased leverage so that it is easier to apply pressure to the tongue.

Another advantage of the angled configuration is that the neck 42 and cleansing head 22 may be inserted far into mouth since the angle configuration resembles the shape of the tongue. Note that due to this angled configuration, only one side of cleansing head 22 is typically flocked and utilized in a tongue cleaning procedure. More particularly, when the handle is angled as shown then it is only usefully used with one orientation for cleaning the far reaches of the tongue as the tongue extends downward in the user's throat. An advantage of having flocked fibers on only one side of cleansing head 22 is that the vertical profile is minimized.

As best shown in FIG. 1E and FIG. 1F, cleansing head 22 has a bare back side and a bare transition to neck 42 beginning at base 25. As discussed above, it is preferred to have a bare back surface in order to minimize the vertical profile. However, in some embodiments both the front surface and the back surface of the cleansing head may be covered. Note that in contrast to head 22', the entire perimeter of cleansing head 22 is covered with flocked fibers such that some fibers extend from the sides 29 of cleansing head 22. This configuration maximizes the ability of cleansing head to clean the tongue.

The brush portion in all of these embodiments is essentially the portion of the tongue cleaning device onto which the fibers are flocked. For example, in the embodiment shown in FIGS. 1A–1H, brush portion 44 is the part of cleansing head 22 that has been flocked. As described in detail below, the cleansing head may have a brush portion that is an integral portion of the cleansing head on which the fibers have been flocked while portions of the cleansing head such as the perimeter are bare as discussed below in reference to head 22'. Alternatively, the brush portion can also be integrally molded into an aperture in the cleansing head as also discussed below in reference to head 22'. Additionally, the brush portion may be separately formed for subsequent insertion into the cleansing head as discussed below in reference to head 22". The brush portions described herein are all examples of brush means for cleaning tongue surfaces via flocked fibers attached to the brush means as the brush means is moved by a handle.

The fibers 46 used to cover or flock cleansing head 22, or more particularly brush portion 44, may have any suitable length and diameter or fineness. One possible length is in a range from about 0.02 inch to about 0.2 inch. Another more preferred length is about 0.04 inch to about 0.175 inch. Another more preferred length is about 0.06 inch to about 0.16 inch. Certain fibers may a length of about 0.125 inch (about 3 mm) or about 0.15 inch (about 4 mm), for example.

The fibers 46 can also have a variety of different lengths. In one embodiment, short and long fibers are flocked onto the cleansing head such that the long fibers are supported by the short fibers. The combination of lengths may assist in cleaning the irregular surfaces of the tongue. The fibers may also have either the same diameter or a plurality of diameters. The range of diameters may be from about 25 denier to about 100 denier, for example. The diameter range may be from about 45 denier to about 100 denier such as about 65 denier to about 100 denier.

When fibers are desired that are considered relatively short and small, fibers may be used that have a length of about 0.065 inch and a diameter of about 45 denier, for example. In contrast, when fibers are desired that are considered to be relatively large and long, the fibers may have a length of about 0.08 inch and a diameter of about 100 denier, for example. The combined use of fibers that are small and short fibers with fibers that are large and long is an example of a useful combination of different types of fibers. Fibers may have a length of about 0.065 inch and a diameter of about 100 denier, for example.

Both synthetic and natural fibers may be used. Suitable synthetic fibers include nylon and polyester fibers while suitable natural fibers include cotton fibers. The fibers may optionally be formed from polypropylene, polyethylene or thermoplastic elastomeric materials having a hardness comparable to polypropylene or polyethylene.

Fibers 46 can be affixed to cleansing head 22, or more particularly brush portion 44, in a variety of different well known methods such as through electrostatic flocking. According to one flocking method, an adhesive is applied to cleansing head 22 where fiber attachment is desired. The adhesive used to attach the fibers to cleansing head 22 is preferably water insoluble, for example, the adhesive may be polyurethane. A polyurethane adhesive has a desired degree of flexibility and water insolubility. An acrylic adhesive may be used that is flexible. Such adhesives are preferably light cured. Other adhesive that may be useful include epoxies and silicones. Another flock adhesive is disclosed in U.S. Pat. No. 5,185,402 which is hereby incorporated by reference. An appropriate quantity of fibers is then contacted with the adhesive material. The adhesive is allowed to harden, thereby securing the fibers to the desired portion. Further information regarding methods for adhering fibers to a cleansing head can be obtained from U.S. patent application Ser. No. 09/702,284 now U.S. Pat. No. 6,450,810, entitled Cushioned, Fiber-Covered Dental Applicators filed on Oct. 30, 2000 and U.S. patent application Ser. No. 09/496,275, now U.S. Pat. No. 6,286,246, entitled Electrostatically Flocked Fishing Lures and Related Systems and Methods, both of which are hereby incorporated by reference. An additional method of fiber attachment is to injection or insertion mold the fibers onto the desired cleansing head. Thus, in one embodiment, the fibers are in a diameter and length which allows injection or insertion molding.

Fibers 46 may extend from cleansing head 22 primarily in a perpendicular configuration as shown. However, the fibers may also extend with other orientations such as a slanted configuration, criss-cross configuration or in a random configuration.

Fibers 46 may have any suitable density. However, the fibers are preferably dense enough such that the tongue is touched by the fibers and not by the cleansing head 22 with the exception of its uncovered perimeter.

Figure 1C:
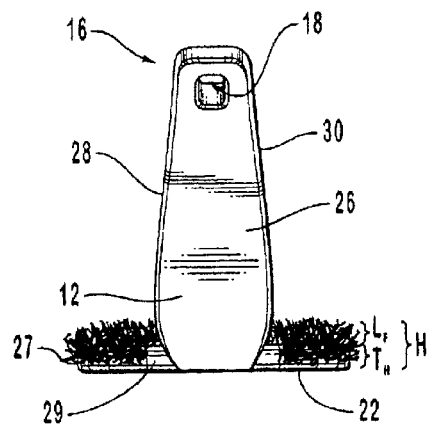
FIG. 1C is a back view of the tongue cleaning device shown in FIG. 1A.
Figure 1D:
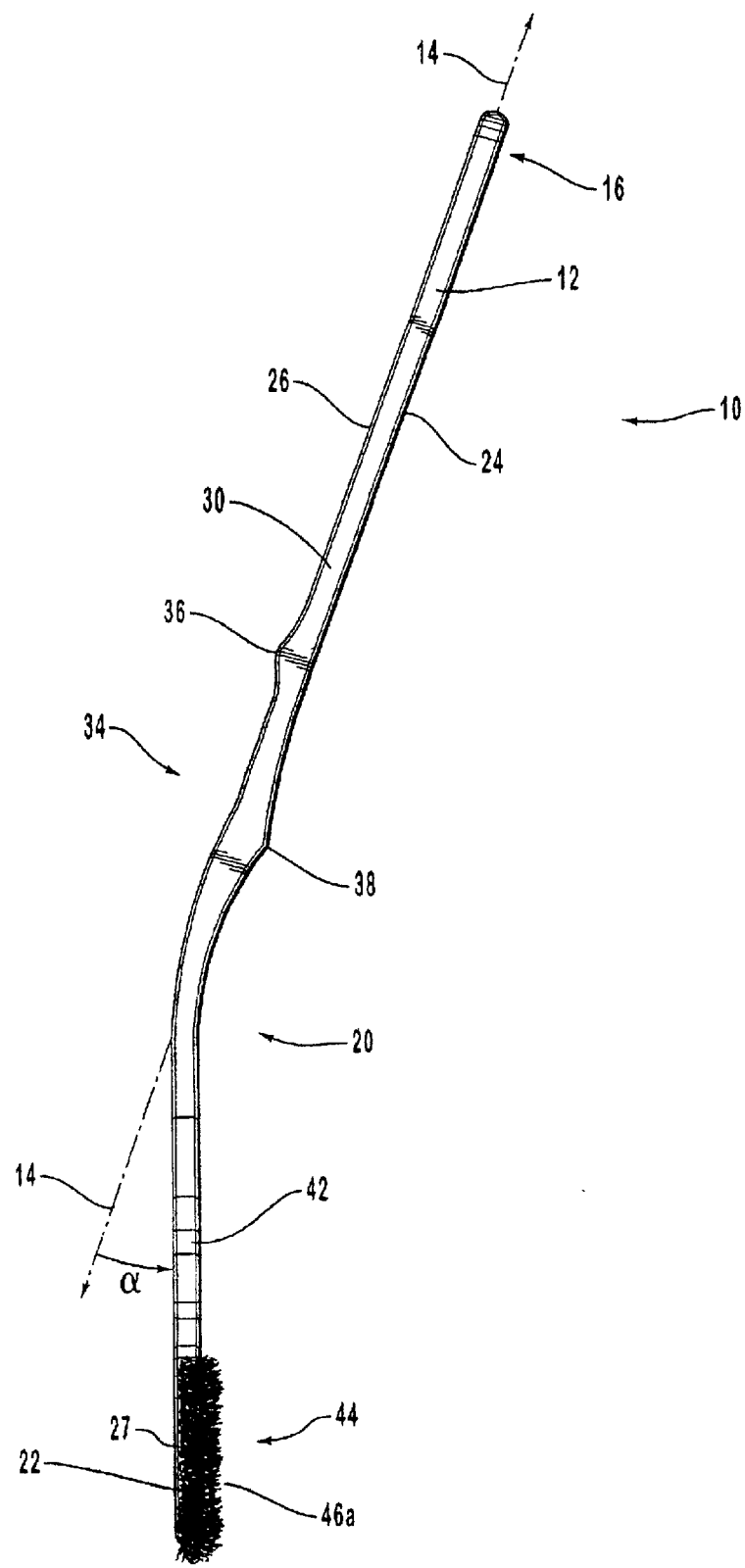
FIG. 1D is a right side view of the tongue cleaning device shown in FIG. 1A, with the left side being a mirror image thereof.
Figure 1G:
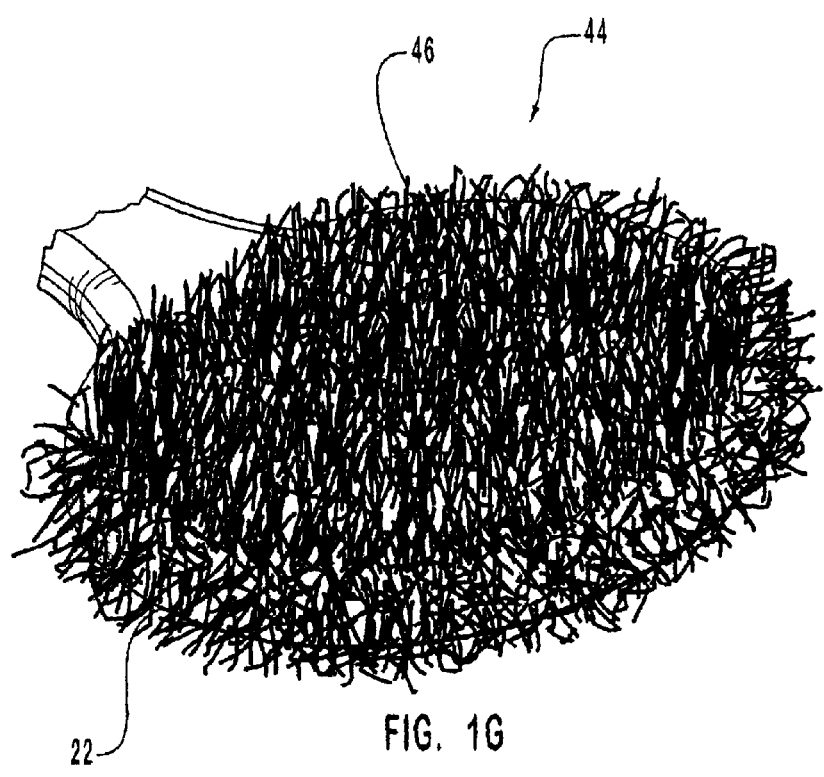
FIG. 1G is an enlarged partial perspective view of the tongue cleaning device shown in FIG. 1A, illustrating the brush portion.
Figure 1H:
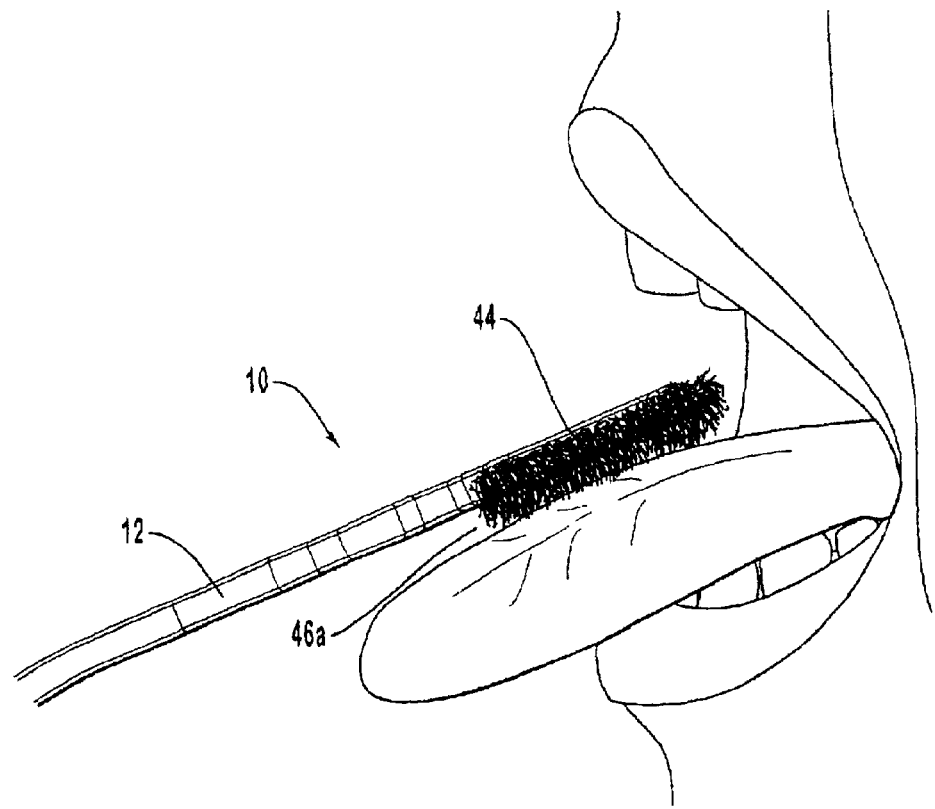
FIG. 1H is an enlarged partial perspective view of the tongue cleaning device shown in FIG. 1A, illustrating the brush portion being pulled across a tongue.

Cleansing head 22 has a thickness denoted in FIG. 1C as $T_H$. The thickness of cleansing head 22 is relatively small to minimize its contribution to the vertical profile or overall height denoted as H in FIG. 1C which is the combination of the thickness of cleansing head 22 and the length that fibers 46 extend beyond cleansing head 22 identified in FIG. 1C as $L_F$. The cleansing head 22 is also preferably sufficiently thick and rigid to enable a user to apply pressure to the tongue by pushing on handle 12 to adequately clean the tongue. The thickness of cleansing head 22 may be in a range from about 0.04 inch to about 0.2 inch, but is preferably in a range of about 0.05 inch to about 0.15 inch, such as 0.125 inch The length that the plurality of flocked fibers 46 extend from said brush portion 44, as denoted in FIG. 1C as $L_F$, is not the length of the individual fibers but the length of fibers 46 as they are situated on brush portion 44. The length denoted in FIG. 1C as $L_F$ may range from about 0.02 inch to about 0.2 inch, for example.

The length of the fibers 46 is preferably minimized such that when combined with the thickness of cleansing head 22, $T_H$, the resulting vertical profile or height identified in FIG. 1C as H, is relatively small. By minimizing the vertical profile or height, the cleansing head can be inserted as far as possible while maximizing the clearance between the cleansing head and the top surface of the mouth. The reduced vertical profile also minimizes the risk of touching the pharynx, soft palate or posterior portion of the mouth in order to avoid causing a gag reflex. It has been found that the vertical profile or height is desirably minimized when it is no greater than about 0.35 inch. However, it is still advantageous for the vertical profile to be even smaller. Accordingly, the combined height, H, resulting from the thickness of cleansing head 22, $T_H$, and the length of fibers 46, $L_F$, is preferably less than about 0.25 inch (less than about 6 mm), is more preferably less than about 0.21 inch. This reduced vertical profile provides a significant advantage over the prior art.

Cleansing head 22 and brush portion 44 are preferably not porous and not compressible. More particularly, cleansing head 22 and brush portion are preferably not resilient like a foam pad. The relatively stiff and nonporous nature of cleansing head 22 and brush portion 44 enables fibers 46 to be urged against the tongue without causing the cleansing head 22 or brush portion 44 to be compressed. The advantage is that the tongue can be cleaned with greater force and yet less effort is required to urge the fibers against one's tongue. Additionally, the nonporous nature of cleansing head 22 and brush portion 44 prevents the retention of moisture that may compromise the hygienic usefulness of the cleaning device.

The embodiment of tongue cleaning device 10 shown in FIGS. 1A–1H, depicts brush portion 44 as being integral with cleansing head 22. In this embodiment, brush portion 44 is the portion of cleansing head 22 from which flocked fibers 46 extend. More particularly, brush portion 44 is all of cleansing head 22 except for its back surface. The brush portion may comprise a smaller section of the cleansing head. For example, the section of the cleansing head comprising the brush portion may appear like brush portion 44' such that there is a bare perimeter around the brush portion. For a cleansing head that is integrally formed from a single material, the configuration of the brush portion depends on the placement of the adhesive used to hold the fibers onto the cleansing head.

The embodiment described in reference to FIGS. 2A–2C has a brush portion 44' which is molded into cleansing head 22' so that brush portion 44' is sealed against cleansing head 22'. Accordingly, the perimeter of its top is not covered with fibers. Another embodiment is described in reference to FIGS. 3A–3D wherein the brush portion 44" is separately formed as a brush insert that is inserted into an aperture in the cleansing head 22". Note that additional fibers can also be adhered onto the remainder or to sections of cleansing head 22' or 22" to provide an appearance like that of cleansing head 22. Note also that these cleansing heads can also be shaped like cleansing head 22. These other embodiments are discussed in detail below.

Any suitable plastic material may be used to form the handle, cleansing head and brush portion. However, the plastic material used may depend on whether the cleansing head and the brush portion are integral or separate components. For example, nylon is a preferred material for an integral head and brush portion. When the brush portion is separate, it may be preferable to use low density polyethylene, polypropylene, copolymers of both polyethylene and polypropylene, or ethyl vinyl acetate.

As indicated above, the brush portion and cleansing head may also be molded together from different materials by conventional molding processes such as a two color molding process. In a two color molding process, one component is molded onto the other. For example, the brush portion may be molded into the aperture of the cleansing head after the cleansing head has been formed to yield a tongue cleaning device 10' as shown in FIGS. 2A–2C. This design is advantageous particularly when it is useful to have components of differing rigidity and flexibility. For example, it may be useful to form the handle from a material such as nylon so that it is relatively hard while the brush portion is formed from a softer plastic material such as low density polyethylene, polypropylene, copolymers of both polyethylene and polypropylene, or ethyl vinyl acetate. Note that while such softer plastic materials are not as rigid as nylon they are still preferably not resilient such as a foam pad and are not porous.

When viewing tongue cleaning device 10' as depicted in the drawings and comparing it with tongue cleaning device 10, the only apparent distinction is mold interface 45. While a mold interface is visible, the components are molded against each other so that there is a seal that prevents ingress. Although, molding the brush portion into the head enables two different materials to be used, it is easier to obtain an optimally minimized vertical profile when the entire tongue cleaning device is integrally molded.

Molding of brush portion 44' into cleansing head 22' can be achieved by any suitable method. For example, cleansing head 22' may have an aperture such as aperture 48" shown in FIG. 3A and be formed to have a configuration corresponding with that of cleansing head 22" described herein below. It is common to rely on holes or other structures to anchor one component to the other as one component is molded onto the other. Accordingly, the plastic material of the component being molded can flow into holes or other structures in a manner that securely locks both components together after the plastic has hardened. If the plastic material used to form the brush portion is deposited into the cleansing head then the cleansing head may have holes or other structures that can function as anchors to hold these components together. Such anchors are examples of interlocking portions. As indicated above, examples of such structures are described in reference to the configuration of cleansing head 22" and brush portion 44" in FIGS. 3A–3D.

It should be understood that the aperture in cleansing head 22' may be formed such as aperture 48" or in other suitable configurations. For example, the aperture may be configured as shown at 48' in FIG. 2C so that the aperture has a solid back as shown in FIG. 1F. Aperture 48' has a sidewall 47 extending up from a flat bottom surface 49. Sidewall 47 is slightly inclined to form an angle less than 90° so that sidewall 47 assists in maintaining brush portion 44' in aperture 48' and acts as an interlocking portion. Similarly, the sidewall may be configured with a lip to act as an interlocking portion. Note that flat bottom surface 49 may also have vent holes of varying configuration for assisting in the molding process.

Even simpler configurations can also be utilized. For example, sidewall 47 can also be formed without an angle as molding the brush portion 44' in the aperture tends to anchor the brush portion due to the seal formed between the material of the brush portion against that of the sidewall. Also, the brush portion can be formed in an aperture having a straight sidewall without a bottom surface.

Figures 3A, 3B, 3C:
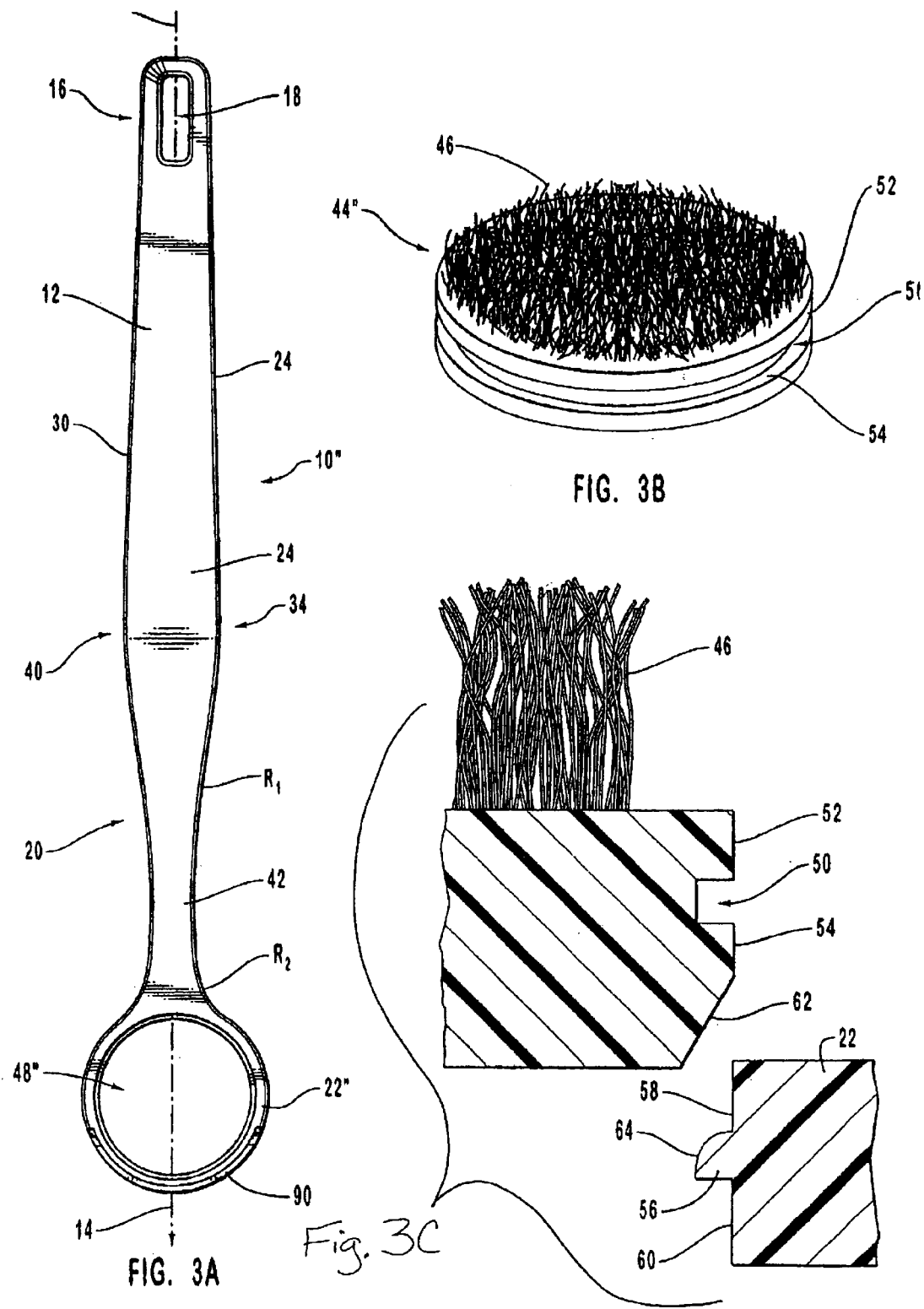
FIG. 3A is a top view of a tongue cleaning device in accordance with another preferred embodiment of the present invention, illustrating a brush portion removed from an aperture in the cleansing head.
FIG. 3B is an enlarged partial perspective view of the insertable brush portion configured for insertion into the aperture of the cleansing head shown in FIG. 3A.
FIG. 3C is an exploded cross-sectional side view of the tongue cleaning device shown in FIG. 3A, illustrating the brush portion and the cleansing head.
Figure 3D:
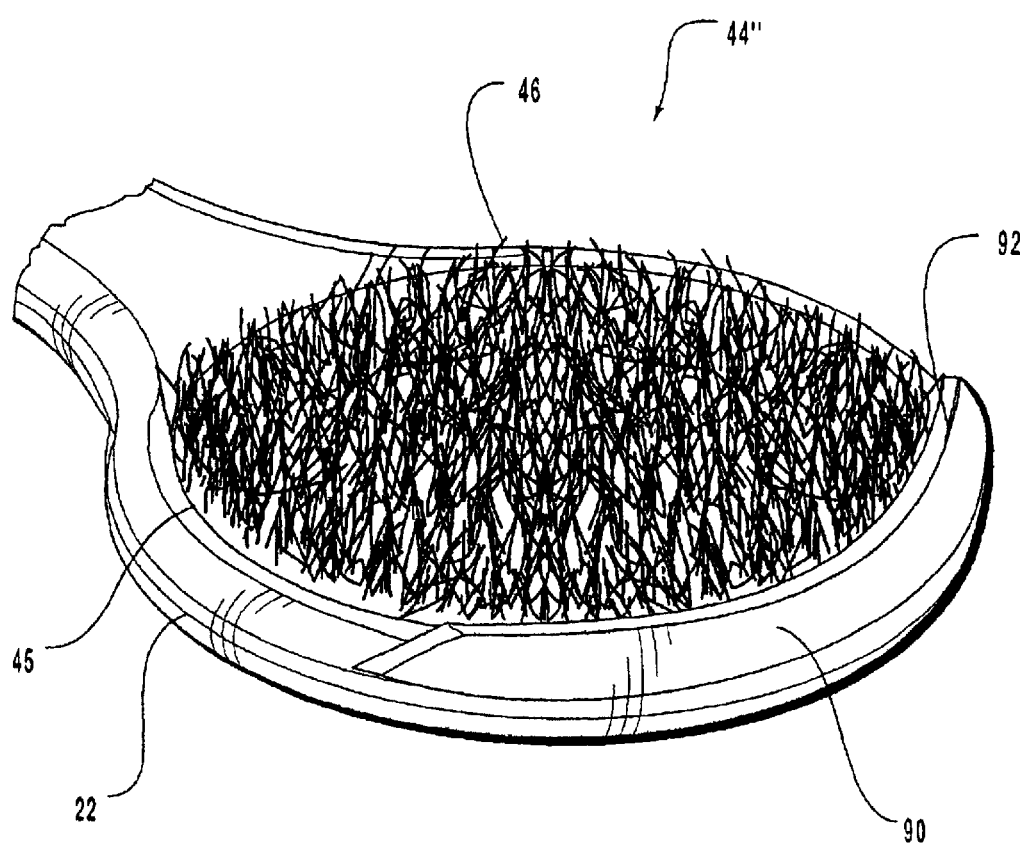
FIG. 3D is an enlarged partial perspective view of the cleansing head after insertion of the insertable brush portion shown in FIG. 3B.

As mentioned above, the cleansing head of the tongue cleaning device may be formed separately from the brush portion. As best seen in FIGS. 3A and 3D, such a cleansing head 22" of tongue cleaning device 10" includes an aperture 48" and a brush portion 44" sized and configured to be inserted and held within the aperture. The aperture 48" and the brush portion 44" may have a diameter of about 1.0 inch for a secure fit of the brush portion within the aperture, but the aperture and brush portion can be larger or smaller.

In greater detail, as best seen in FIGS. 3B and 3C, the brush portion 44" includes a groove 50 that is located between a first ridge 52 and a second ridge 54. The cleansing head 22" includes a radially inwardly extending flange 56 that is positioned between a first inner surface 58 and a second inner surface 60. The brush portion 44" is configured to be snap-fit into the aperture 48" to securely attach the brush portion to the cleansing head 22". Preferably, the second ridge 54 of the brush portion 44" includes an angled surface 62 and the inwardly extending flange 56 includes a curved upper surface 64 to facilitate the snap-fit connection. The snap-fit connection preferably requires a significant amount of force to insert the brush portion 44" into the aperture 48" to create a generally permanent connection. Alternatively, the snap-fit connection may be configured to allow the brush portion 44" to be removably attached to the cleansing head 22". Thus, for example, this allows the brush portion 44" to be replaced if worn or to use brush portions with different types or fiber configurations. It will be appreciated that the brush portion 44" can be attached to the cleansing head 22" by any suitable means, including an interference fit, sonic or ultrasonic welding, adhesives, bonding, and the like.

Groove 50 of brush portion 44" is an example of an interlocking portion of brush portion 44". Flange 56 of cleansing head 22" is an example of an interlocking portion of cleansing head 22". Groove 50 and flange 56 are also examples of means for interlocking the brush portion and the cleansing head together in a manner such that the brush portion is received within the aperture of the cleansing head while preventing the subsequent removal of the brush portion. The advantage of this configuration is that brush portion 44 is so tightly held by cleansing head 22 that ingress is minimized of water, saliva, etc. which can lead to bacterial growth within the tongue cleaning device. Note that when the mated configuration of groove 50 and flange 56 is utilized, the interlocking portion of the cleansing head extends into the interlocking portion of the brush portion. In other embodiments, this configuration can be reversed such that the interlocking portion of the brush portion extends into the interlocking portion of the cleansing head. The interlocking portions described above in reference to FIGS. 2A–2C are also examples of interlocking means.

As shown in FIGS. 2A–2B, an optional scraper 90 is attached at the end of the cleansing head 22' of the tongue cleaning device 10'. The scraper 90 is used to scrape and remove foreign material and debris from the outer surface of the tongue. The scraper 90 may also be used to scrape and remove debris loosed by the brush portion 44. As best seen in FIG. 2B, the scraper 90 has a rounded upper surface 92 and it has a height of about 0.070 inch, which allows the scraper to clean the posterior portion of the tongue without touching the pharynx or soft palate. Thus, the scraper 90 minimizes the possibility of triggering the gag reflex. The scraper 90 is aligned with the outer surface of the cleaning head 22' to prevent debris and other material from accumulating between the end of the cleansing head 22' and the scraper. The scraper 90 is also positioned proximate the brush portion 44' to prevent debris and other material from accumulating between the fibers 46 and the scraper 90. The scraper 90 preferably extends about 120° about the circumference of the cleaning head 22', but the scraper could be larger or smaller. It will be understood that the scraper 90 could have any suitable dimensions and the tongue cleaning device does not require the scraper.

In sum, the tongue cleaning device 10 quickly and efficiently cleans the tongue without eliciting the gag reflex. Additionally, the fibers 46 remove food and other debris from the various ridges, grooves, furrows and other surfaces of the tongue without damaging or irritating the tongue. Further, the scraper 90 can also be used to remove foreign matter from the outer surface of the tongue. As described below, the tongue cleaning device 10 is easy to use and operate.

In operation, the user grasps the tongue cleaning device 10 by the handle 12 with either hand. The cleansing head 22 of the tongue cleaning device 10 is inserted into the mouth of the user with the fibers 46 facing downward, towards the dorsal surface of the tongue. The fibers 46 are placed in contact with the tongue and the tongue cleaning device 10 is moved relative to the tongue with the fibers engaging the dorsal surface of the tongue. The fibers 46 advantageously loosen and clean debris, plaque, food, etc. from the various grooves, furrows, papillae and the like from the outer surface of the tongue. That is, the fibers 46 independently contact and scrub the outer surface of the tongue. The scraper 90 can then be used to move the loosened debris and particles. Alternatively, the scraper 90 can be used to contact the tongue to assist in loosing the debris and other particles on the tongue. The user can then remove the debris from his or her mouth, for example, by rinsing, expectorating or swallowing.

Significantly, the cleaning process allows the dorsal surface of the tongue to be quickly and efficiently cleaned. Additionally, a gag reflex is not triggered because of the relatively small profile of the tongue cleaning device. Further, the large contact area of the tongue cleaning device 10 speeds the cleaning process and the fibers 46 independently contact and clean the varied outer surfaces of the tongue.

Figure 4:
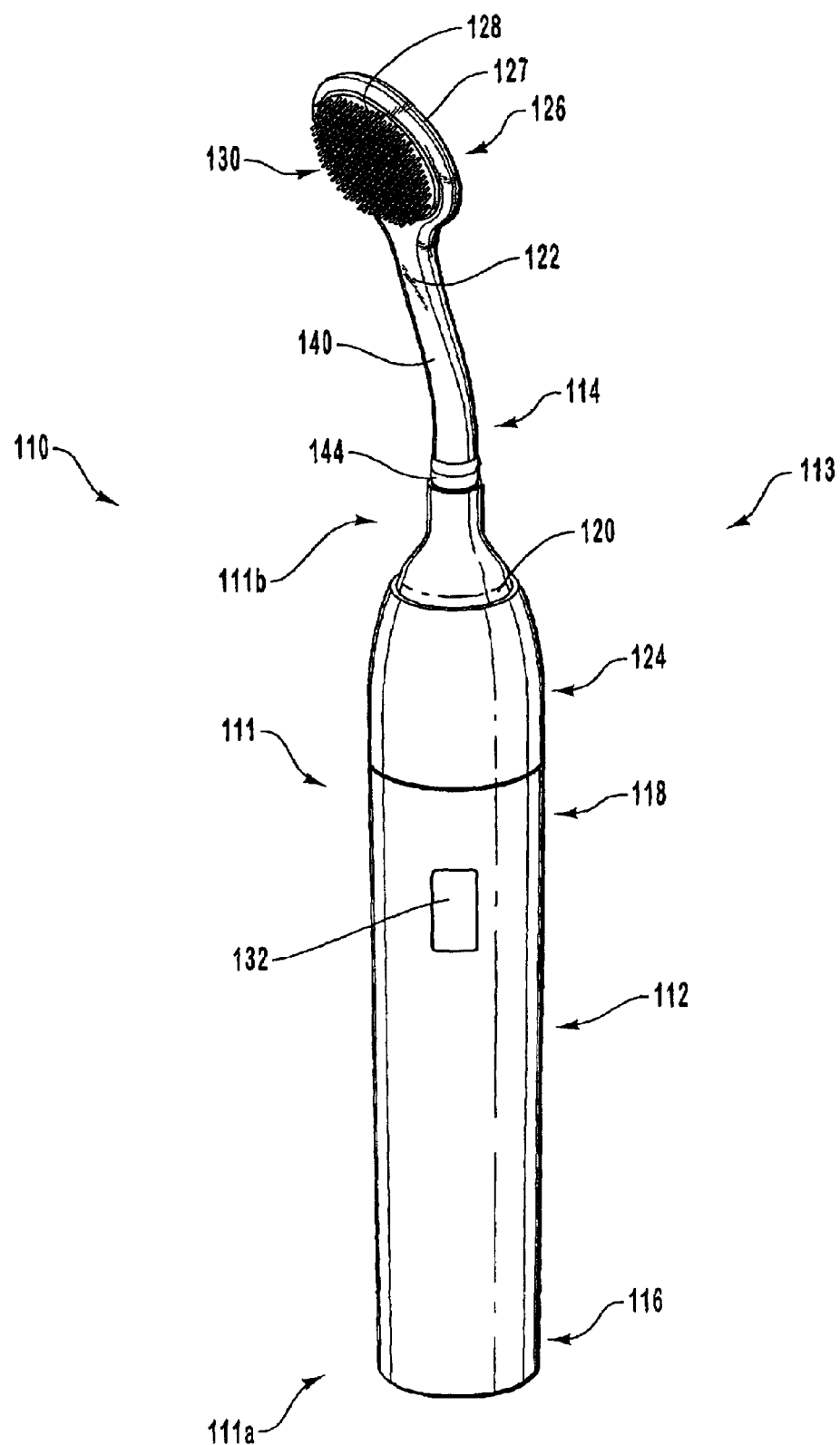
FIG. 4 is a view of a powered tongue cleaning device of the present invention.

With reference now to FIG. 4, an embodiment of a powered, portable, hand-held tongue cleaning device 110 of the present invention is shown. This device is very useful in cleaning the tongue of a patient and can be used by a dental practitioner or by an individual at home or in a variety of settings to make tongue cleaning more convenient. Making such cleaning more convenient increases the likelihood that the user will engage in regular brushing habits. The powered tongue cleaning device 110 enables the user to clean his or her tongue while performing less work compared to manually scrubbing the tongue. Instead, the user can place the device 110 adjacent the user's mouth with the brush head inside the mouth and against the tongue, then actuate the device to thereby conveniently clean the user's tongue.

The powered device is specifically designed for cleaning of the tongue. Thus, the configuration of the brush head (which fits inside the user's mouth) and arm coupled thereto thereof minimize the elicitation of a gag reflex when the device 110 is used to clean the tongue. Furthermore, the curvature of the brush head and arm allows the brush head to fit conveniently within the oral cavity.

Tongue cleaning device 110 comprises a motorized device 113 coupled to a brush head 126 to thereby move the brush head 126 in a desired fashion and clean the tongue of a user. Motorized device 113 comprises a housing 111 having a motor assembly coupled thereto and arm 122 coupling the brush head 126 to the housing 111. Each of these components will now be described in additional detail.

Housing 111 is configured to enable a user to grasp the tongue cleaning device as the tongue cleaning device is directed by the user to facilitate a tongue cleaning procedure in the user's mouth. Housing 111 has a first, proximal end 111a and a second, distal end 111b. Housing 111 of FIG. 4 comprises a hollow handle 112 that is coupled to tip 114, as shown in FIG. 1. Handle 112 has a first, proximal end 116 and a second, distal end 118.

Housing 111 further comprises (i) a hollow tip casing member 120 that is part of a removable tip 114; and (ii) a removable, hollow neck 124.

Tip 114 comprises tip casing 120, a lever arm 140 comprising a distal, curved distal lever portion 122, and brush head 126 coupled to distal lever portion 122. Only the distal lever portion 122 portion of lever arm 140 is shown in FIG. 4.

Removable neck 124 selectively seats onto tip casing 120 and also selectively threads onto distal end 118 of handle 112, thereby selectively coupling tip 114 to handle 112. Thus, keeping in mind that a variety of different housing configurations may be employed in the present invention, housing 111 of FIG. 4 comprises handle 112, tip casing 120 and neck 124. Neck 124 selectively couples tip casing 120 to handle 112, thereby selectively coupling the overall assembly that forms tip 114 to handle 112. This enables a variety of different interchangeable tips 114 having different brush heads 126 thereon to be coupled to handle 112.

Brush head 126 is coupled to distal lever portion 122 of curved lever arm 140, which is coupled to housing 111. Head 126 may be integrally coupled to portion 122 or otherwise coupled thereto. Brush head 126 of FIG. 4 comprises a cleansing head 127 and a plurality of fibers 130 coupled thereto, such as through electrostatic flocking. Cleansing head 127 (which may comprise any of the cleansing heads described herein, including those incorporated by reference) is attached to the curved distal lever portion 122 of elongate tip 114. Cleansing head 127 is sized and shaped to fit conveniently within the user's mouth.

In the embodiment of FIG. 4, fibers 130 are coupled to a front surface of the cleansing head 126, namely to the brush portion 128 of the cleansing head 127. Fibers 130 are adhered onto said brush portion 128 by an adhesive, such as through the use of electrostatic flocking.

The term "brush head," as used in this specification and the appended claims, refers to (i) a cleansing head 127; and (ii) any bristles coupled thereto, such as fibers 130, fingers, or any other type of bristles extending from a brush portion 128 of the cleansing head 127. The brush portion 128 is the portion on which the brushing members (e.g, fibers, fingers, or other types of bristles) are mounted and may be integral with or otherwise coupled to the remaining portion (e.g., the outer rim) of the cleansing head 127.

The bristles that may be coupled to the brush portion of the cleansing head disclosed herein may comprise a variety of different bristles, such as flocked fibers (e.g., electrostatically flocked fibers), plastic fibers, fingers, stiff bristles, flexible bristles, bristles that are embedded into the brush portion of the cleansing head, bristles that are adhered with an adhesive to the cleansing head, bristles that are formed integrally with the brush portion of the cleansing head, and a variety of other bristles that may be employed to clean the tongue.

Brush head 126 is thus configured to clean tongue surfaces s brush head 126 is moved against the surface of the tongue. The brush head of the present invention used in association with the powered components disclosed herein may have a variety of configurations, such as any of the configurations disclosed above (e.g., in FIGS. 1A–3D), disclosed in FIGS. 4–10, and/or in (i) U.S. patent application Ser. No. 09/801,974, now U.S. Pat. No. 6,625,839, entitled "Flocked Tongue Cleaning Device and Related Method, tiled Mar. 8, 2001, (ii) U.S. patent application Ser. No. 09/511,827 entitled Tongue Cleaning Device and Related Methods, which was filed on Feb. 24, 2000, which is now abandoned, or (iii) U.S. patent application Ser. No. 09/484, 302, which is also now abandoned, entitled Tongue Brush which was filed on Jan. 18, 2000 on behalf of Dan E. Fischer and Bruce S. McLean, each of which is incorporated herein by reference. Thus, each of the cleansing heads disclosed herein along with their associated bristles coupled thereto may be employed herein as a brush head to form a powered tongue cleaning device.

Brush head 126 has a height that is substantially less than the width thereof. For example, brush head 126 has a height that is no greater than about 0.35 inch and preferably less, as discussed below. Thus, the configuration of brush head 126 minimizes the elicitation of a gag reflex when the device 110 is used to clean the tongue. Furthermore, brush head 126 has a substantially flat profile, which also minimizes the elicitation of a gag reflex when the device 110 is used to clean the tongue. As discussed above with reference to FIG. 1C, cleansing head 127 and said plurality of fibers 130 have a combined height such that brush head 126 has a relatively low vertical profile to minimize the elicitation of a gag reflex when the device is used to clean the tongue.

The curvature of distal lever arm 140 coupled to brush head 126 also minimizes the elicitation of a gag reflex and enable distal lever portion 122 of arm 140 to fit within the mouth of the user. Distal lever portion 122 has a generally flat shape and is significatly thinner than brush head 126, thereby enabling brush head 126 to be placed conveniently within a user's mouth. Curved arm 140 enables the brush to extend far enough to reach one's throat and follow the curvature of the tongue as it extends down into the throat FIG. 5 demonstrates housing 111 in an exploded view with handle 112 separated from tip 114 and neck 124. As shown in FIG. 5, and as mentioned above, neck 124 selectively couples tip 114 to handle 112, such as by coupling internal threads of neck 124 to the external threads 158 of handle 112. A ridge 152 of an elongate member 154, which is an integral part of casing 120 slides into a track 156 of handle 112 to thereby orient tip 114 onto handle in such a manner that the components of handle 112 and the components of tip 114 are aligned.

FIG. 6A demonstrates a cross sectional view of tip 114 and neck 124. With reference now to FIGS. 5 and 6A, brush head 126 is coupled to tip casing 120 of housing 111 by a two-part lever arm 140 that is coupled to casing 120 and brush head 126. The movement of lever arm 140 causes the movement of brush head 126, thereby cleaning the tongue of a user who places the brush head 126 against his or her tongue.

As shown in FIG. 6A, curved lever arm 140 comprises: (i) a proximal lever portion 143 that is coupled to casing 120 and distal lever portion 122 that is coupled to proximal lever portion 143. In one embodiment, the housing 111 and distal lever portion 122 comprise a material that can be held by a user and placed in the mouth of the user, such as a nonmetallic (e.g., polymeric) material, such as nylon, polypropylene, polyethylene, for example, while the proximal lever portion 143 comprises a metallic material. The nonmetallic material may be molded on the metallic portion or the metallic portion may be adhered to the nonmetallic portion through an adhesive or mechanical coupling.

Proximal lever portion 143 of lever arm 140 extends through a passageway of casing 120. A seal 144 (e.g., a circular elastomeric seal) seals the opening between tip casing 120 and distal lever portion 122.

In one embodiment, an arm of the present invention that couples to a brush head is immovably affixed to a vibrating housing in order to cause brush head 126 to vibrate (e.g., refer to the discussion relating to FIG. 7 below).

In the embodiment of FIGS. 5 and 6, however, lever arm 140 is movably coupled to housing 111 such that the lever arm 140 can be vibrated. As shown, lever 140 is coupled to upper and lower pivot members 170, 172 that movably couple lever arm 140 to a diaphragm 174 (e.g., a circular or half circular metal diaphram) coupled firmly within tip casing 120 such that lever arm 140 can vibrate within casing 120 when a rear plate 150 of lever arm 140 is moved.

Lever arm 140 and its associated components may be the same as or similar to the lever and associated components described in U.S. Pat. Nos. 5,815,872, 5,378,153, and 5,263, 218, for example, each of which are incorporated herein by reference. However, lever arm 140 may be coupled to casing 120 in a variety of different manners.

Lever arm 140 can also be moved in a variety of different manners (thereby moving brush head 126). Tongue cleaning device 110 further comprises means for moving lever arm 140 such that brush head 126 moves against the surface of the tongue as the user holds the housing of the device.

For example, in the embodiment of FIG. 5, one example of a motor assembly configured to move lever arm 140 comprises a motor 160, actuated by on/off button 132, and a power source 162 that provides power, e.g., electrical power to motor 160. This motor assembly is an example of a means for moving lever arm 140.

A motor assembly of the present invention configured to move lever arm 140 or otherwise move brush head 126 may comprise a variety of different motor assemblies, such as a typical mechanical motor, a cam assembly, a magnetic assembly, a sonic or ultrasonic mechanism, a vibrating motor, electromechanical motors, electric motors, and a variety of different motor assemblies known to those skilled in the art. Each of these are examples of means for moving arm 140.

As shown, the motor 160 may be disposed within the housing 111, as may at least part of the power source 162. In one embodiment, power source 162 comprises one or more rechargeable batteries and a charging assembly such that the batteries may be recharged when placed on or near or coupled to a charging source. Optionally, the power source 162 may include a cord that is coupled to an electrical outlet. In this embodiment, at least a portion of the power source (i.e. the battery) is mounted within the housing while the recharging source is located outside the housing. Thus, in one embodiment, the power source comprises a rechargeable battery (or a plurality of batteries) disposed within the housing, a charging assembly disposed inside the assembly and electrically coupled to the battery configured to be used in associated with a charging unit disposed outside the housing and configured to charge the battery through the charging assembly. However, the power source 162 may comprise a variety of different power sources, such as one or more replaceable batteries, a cord coupled to handle 112 and extending to a power outlet, and/or a variety of different power sources.

Motor 160, power source 162, and on/off button 132 thus comprise an example of a motor assembly that vibrates lever arm 140 coupled to brush head 126. This motor assembly is an example of a means for moving arm 140.

In the embodiment of FIGS. 5 and 6, upon vibration of lever arm 140, which occurs upon actuation of the motor assembly, brush head 126 begins to vibrate. Such vibration of brush head 126 may occur in a variety of different motions, such as a back and forth motion, a side to side motion, a circular motion, an irregular motion and/or a variety of different motions that enable brush head 126 to cleanse the tongue. Thus, upon placing brush head 126 within a patient's mouth adjacent the patent's tongue, brush head 126 cleans the patient's tongue.

Movement of brush head 126 may also be accomplished through a variety of different motions, such as oscillation or spinning the brush head in a circular manner, for example. These motions can be achieved by coupling a brush head of the present invention to a variety of different motorized devices that enable such movement.

A more specific example of a motor assembly of the present invention will now be given. In the embodiment shown in FIGS. 5, 5A and 6, the motor assembly comprises (i) a motor 160 (ii) first and second permanent magnets 146, 148 (FIG. 5A) coupled to a rear plate 150 of lever arm 140; and (iii) power source 162, such as one or more rechargeable batteries and recharging assembly within housing 111 electrically coupled to the one or more batteries. Motor 160 disposed within handle 112 comprises an electromagnetic drive circuit disposed within the housing 111 that moves the magnets, thereby vibrating lever arm 140 and causing brush head 126 to vibrate. In one embodiment, magnets 146, 148 coupled to rear plate 150 of lever arm 140 are alternately repulsed and attracted by the electromagnetic drive circuit, such as discussed in U.S. Pat. Nos. 5,815,872, 5,189,751, 5,378,153, 5,263,218, 5,544,382, 5,796,325, 5,994,855, and 5,305,492, each of which are incorporated by reference herein. The alternate attraction and repulsion of the magnets coupled to the lever arm 140 causes the lever to vibrate, thereby causing brush arm 143 to vibrate.

In one embodiment, the electromagnetic drive circuit is formed through the use of a motor 160 in the form of an electromagnet and an oscillator that produces a signal that is applied to a coil of the electromagnet, while power source 162 comprises a battery that provides power to the oscillator. Thus, in one embodiment, a means for moving lever arm 140 comprises a pair of magnets 146, 148, an electromagnet, an oscillator, and a power source (also known as a pair of permanent magnets, an electromagnet and a battery/oscillator). Examples of such means for moving lever arm 140 comprising these components, are provided in U.S. Pat. Nos. 5,815,872, 5,378,153, 5,263,218, 5,189,751, 5,544,382, 5,796,325, 5,994,855, and 5,305,492, which are incorporated herein by reference, as discussed above. The components described in these patents may be employed in the present invention to move lever arm 140 or a similar lever coupled to a brush of a present invention.

In one embodiment, the amplitude and frequency of the electromagnetic circuit are designed so as to produce effective scrubbing, yet low enough as to not sound irritating to the user. Rear plate 150 may comprise an iron backing member, for example, to allow effective mounting of the magnets thereon.

Thus, in one embodiment the tongue brush is a battery-powered, magnetically driven tongue brush. In the embodiment shown, no contact is necessary between lever arm 140 and the electromagnet. Consequently, handle 112 can be sealed with a solid wall between motor 160 and lever arm 140. In one specific embodiment, pivot arms 170, 172 comprise a hardened steel material, e.g., music wire that allow lever 140 to pivot within housing 111.

This is one example of a means for moving lever 140, and consequently brush head 126. However, as emphasized, a variety of other motor assemblies can accomplish this purpose, such as a simple vibrating motor disposed within a housing that has an arm coupled thereto, to which a brush head such as brush head 126 is coupled. Upon actuation of the motor, the arm vibrates, thereby vibrating the brush head 126. Brush head 126 may be integrally coupled to arm 122 or coupled thereto in a variety of different manners.

With reference now to FIG. 6B, in one embodiment, brush head 126a is coupled to an arm 122a that is selectively mounted a lever. Thus, brush head 126a can be removed from a particular cleaning device and and replaced with another brush head. A friction fit or an adhesive, for example, may be employed to couple arm 122a to another lever portion, such as proximal lever portion 143 of FIG. 6A, for example. The lever portion 143 may fit within internal passageway 145 shown in cross section. An arm having such an internal passageway 145 (e.g., an arm long enough to be conveniently held by a user) can also be used as the handle of a manual brush for manual brushing of the tongue.

Brush head 126a comprises a plurality of fibers 130a electrostatically flocked onto a first (i.e., front) surface, namely brush portion 129 of cleansing head 110a of the present invention, and has curved arm 122a coupled integrally thereto. Second (i.e. rear surface 131 is tapered, as discussed below. However a brush head mounted to a removable arm may be the same as or similar to the other brush head embodiments disclosed herein, for example.

In one embodiment, arm 122a is selectively mounted on the lever arm disclosed in U.S. Pat. No. 5,263,218, (see column 4, line 26) relating to a toothbrush, thereby forming a mouth cleaning system that can comprise a tongue brush and/or toothbrush, either of which may be selectively employed on the lever arm disclosed therein to clean the teeth and/or tongue. In yet another embodiment of the present invention, arm 122a or another brush head or brush head/arm combination disclosed herein is configured to permanently or selectively replace a toothbrush head mounted on a vibrating tooth brushing device, such a the sonic tooth brush device presently sold under the name SONICARE and sold by Philips Oral Healthcare, Inc., 35301 SE Center Street, Snoqualmie, Wash., 98065, and advertised at www.sonicare.com. The use of a SONICARE vibrating mechanism along with a toothbrush head and arm 122a and head 126a combination is thus another example of a system for cleaning the mouth, i.e. the teeth and/or tongue.

Figure 7:
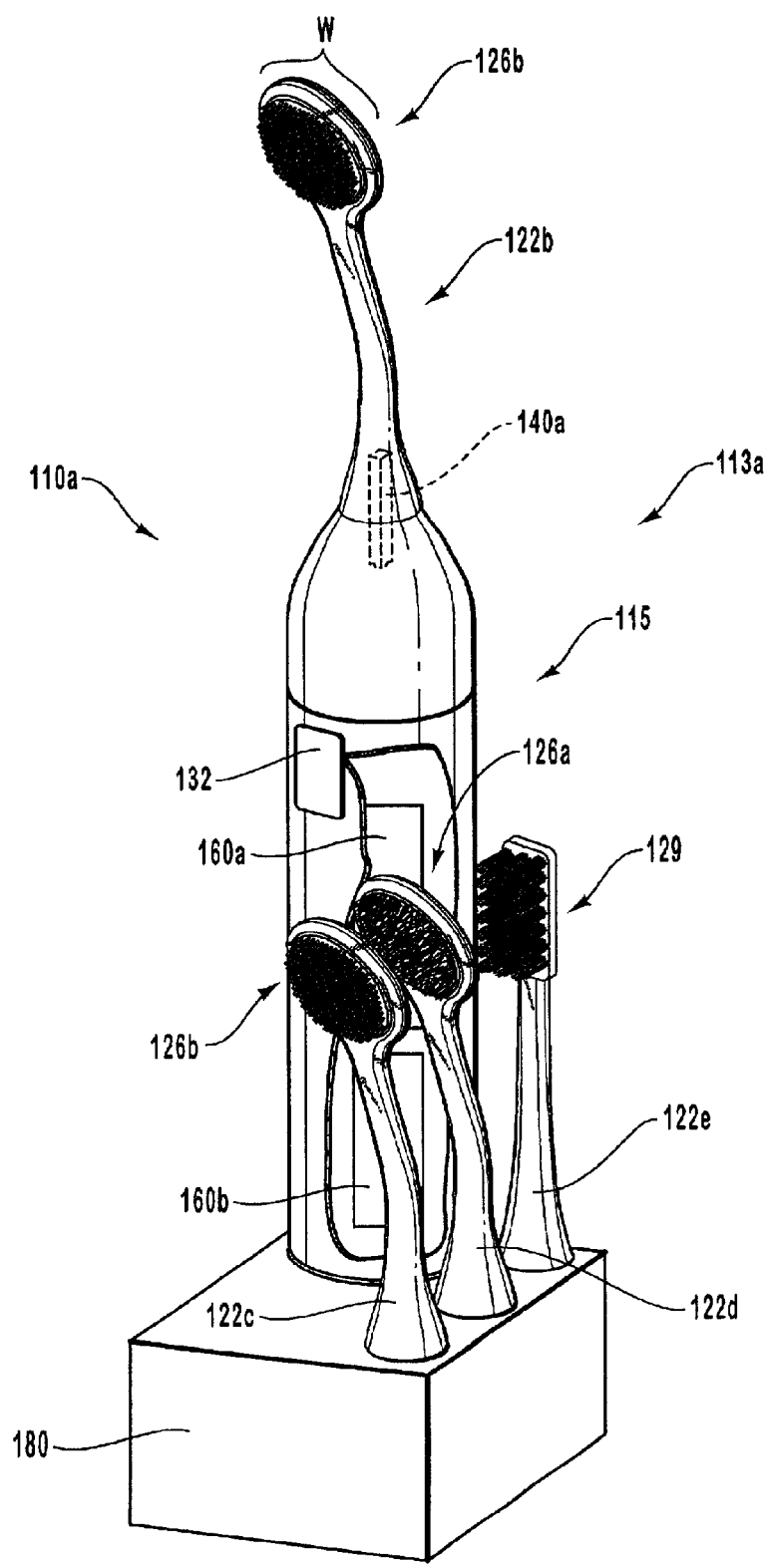
FIG. 7 is a view of yet another powered tongue cleaning device mounted in a recharging unit and having a variety of different tips adjacent thereto, the tips selectively replacing the tip shown in the device. The recharging unit thus serves as a convenient container for the replacement tips.

FIG. 7 shows another example of a powered tongue cleaning device 110a of the present invention, with the housing 115 being placed in a charging unit 180 to recharge the power source. The charging unit 180 and a rechargeable battery assembly may be the same as or similar to the devices disclosed in U.S. Pat. Nos. 5,544,382, 5,796,325, and/or 5,994,855, for example, which are incorporated herein by reference.

Also as shown in FIG. 7, a variety of different brush heads 126a–b with their associated arms 122c–d may be mounted on or adjacent the charging unit 180 as replaceable tips, such that the arms are interchangeable with arm 122b.

Arm 122b is coupled to motorized device 113, which may comprise a variety of different motor assemblies configured to move arm, such as a typical mechanical motor, a cam assembly, a magnetic assembly, a sonic or ultrasonic mechanism, a vibrating motor, electromechanical motors, electric motors, and a variety of different motor assemblies known to those skilled in the art. Each of these are examples of means for moving arm 122b.

Arm 122b may be configured in accordance with a variety of different arms that are coupled to a vibrating device, for example. Arm 122b is coupled to brush head 126b, which may also comprise a variety of different components, such as electrostatically flocked fibers. An arm 122e having a tooth brush head 129 coupled thereto may also be employed for convienient switching between a tongue brush and a tooth brush. Arm 122e may be selectively coupled to housing 115 and/or portion 143 of lever 140 (e.g., wherein the lever is straight, rather than curved), for example. Thus, FIGS. 6A, 6B and 7 feature examples of a portable, powered, hand-held system for cleaning the mouth.

Arm 122b may be coupled to housing 115 in a variety of different manners. For example, arm 122b may have the configuration of a removable arm of any of a variety of typical electromechanical tooth brushes. For example, the arm may also be coupled to the body of the electromechanical tooth brush through the use of interlocking members on the lower portion of arm 122b and housing 115, such that the lower end of arm 122b is placed inside housing 115, then turns within a corresponding channel in housing 115 to mount arm 122b within housing 115.

Furthermore, arm 122b may be moved in a variety of different manners. The brush head of the brush may reciprocate back and forth, for example. The arm 122b may also move about its axis. The arm may also be vibrated by the vibration of housing 115 resulting from a vibrating motor therein.

Device 110a may thus comprise a housing having a vibrating motor 160 therein, for example (which is coupled to a power source 160b, for example) to move arm 122b and therefore head 126b. However, as mentioned, motor 160 may comprise a variety of different motors, such as a mechanical motor, a cam assembly, a magnetic assembly, a sonic or ultrasonic mechanism, electromechanical motors, electric motors, and a variety of different motors known to those skilled in the art. Each of these are examples of means for moving arm 140.

Arm 122b is not necessarily movably coupled to housing 115, but may be immovably affixed thereby, yet move upon vibration of the housing 115, for example. In yet another embodiment, arm 122b is coupled to an optional lever arm 140a shown in phantom lines extending from housing 115. In one embodiment, however, no such lever arm 140a is employed.

The term "arm" as used herein refers to any member that is coupled to the brush head of the powered tongue cleaning device and to a housing that is grasped by a user. The arm may thus be integral with the housing grasped by the user or may be coupled thereto. Preferably, the arm is thinner than the brush head and housing, as shown.

Returning now to FIGS. 6A and 6B and as discussed above, brush head 126 (and/or 126a) of the prevent invention has a generally flat profile and has a height "H" or "$H_1$" that is no greater than about 0.35 inch. This configuration of the brush minimizes the elicitation of a gag reflex when the device is used to clean the tongue. However, as discussed above with reference to FIG. 1C, it is still advantageous for the vertical profile to be even smaller. With reference to FIG. 6B, the height "$H_1$" resulting from the thickness of the cleansing head 110a and the length of fibers 130a is preferably less than about 0.25 inch, and is more preferably less than about 0.21 inch. In one embodiment, the length of the fibers of the brush head, is about 0.02 inch to about 0.2 inch, e.g., about 0.01 inch to about 0.1 inch, such as about 0.065 inch or about 0.08 inch.

Furthermore, in one embodiment, the width "W" of brush head 126, 126a, 126b or 126c or any other brush head herein, 126a may be in the range of about 0.5 inch to about 2 inches, preferably about 0.75 inch to about 1.75 inch, more preferably about 1 inch to about 1.5 inch. These widths are preferable because a wide brush enables a user to brush the tongue more quickly, also minimizig the elicitation of a gag reflex when the device is used to clean the tongue. For example, the tongue may be about 2 to about 2.5 inches in a given person, although sizes may vary. A brush having a width of more than about 1 inch is only required to make two or three brushes along the surface of such a tongue to clean the entire tongue, and thus is a significant aspect of the present invention.

In one embodiment, the height of the brush head 126 is about 0.03 inch to about 0.35 inch. For example, in the 0.03 inch embodiment, 0.015 inch may be taken up by the cleansing head while 0.015 inch is taken up by fibers and adhesive.

This substantially greater width than height has many advantages. In one embodiment, the ratio of the height to the width of the brush head is according to the following ratios. In one embodiment, the ratio of the height to the width (i.e., height/width) of the brush head is in the range of about 0.015 to about 0.7, preferably, in the range of about 0.017 to about 0.46 and more preferably, about 0.02 to about 0.35.

In addition, in one embodiment, the length, "L" of the brush head herein is in the range of about 0.25 inch to about 2 inches, preferably about 0.5 inch to about 1.5 inches, more preferably about 0.7 inch to about 1.25 inch.

Also with reference to FIG. 6B, in one embodiment, the cleansing head 110a is tapered on a surface 131 opposite the brush portion 129 of the cleansing head 110a such that the profile of the overall brush head 126a is as low as possible. For example, in one embodiment, the thickness of brush head 126a is about 0.125 inches thick at the proximal end 176 (which is integrally coupled to arm 122a) of the cleansing head 126a and tapers to about 0.06 inch at the distal tip 178 of cleansing head head 126a. Thus, in one embodiment, the distal tip of the cleansing head is less than 90% the thickness of the proximal tip of the cleansing head, preferably less than 75% the thickness of the proximal tip of the cleansing head, preferably less than 50% the thickness of the proximal tip of the cleansing head. This tapering also helps to prevent triggering a gag reflex.

Figure 8:
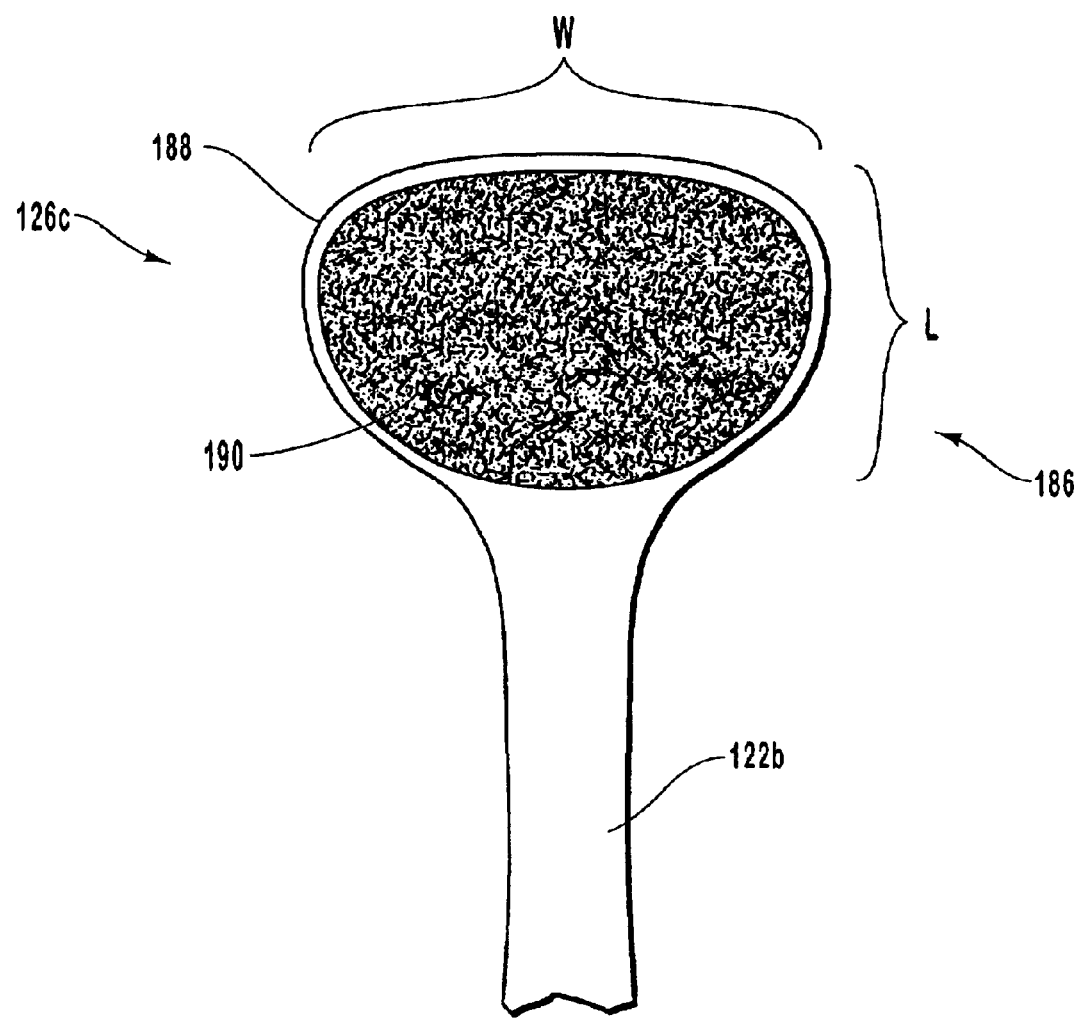
FIG. 8 is a view of another cleansing head of the present invention, the cleansing head configured to receive a variety of different bristles thereon.

With reference now to FIG. 8, yet another example of a cleansing head 186 that may be employed in the present invention is shown. Cleansing head 186 demonstrates that the width "W" of the cleansing head may be significant, e.g., more than about 1 inch in one embodiment. In fact, in one embodiment, the width "W" of cleansning head is about 1.28 inch. Rim 188 may be employed to keep adhesive within brush portion 190 of cleansing head.

Figure 13A:
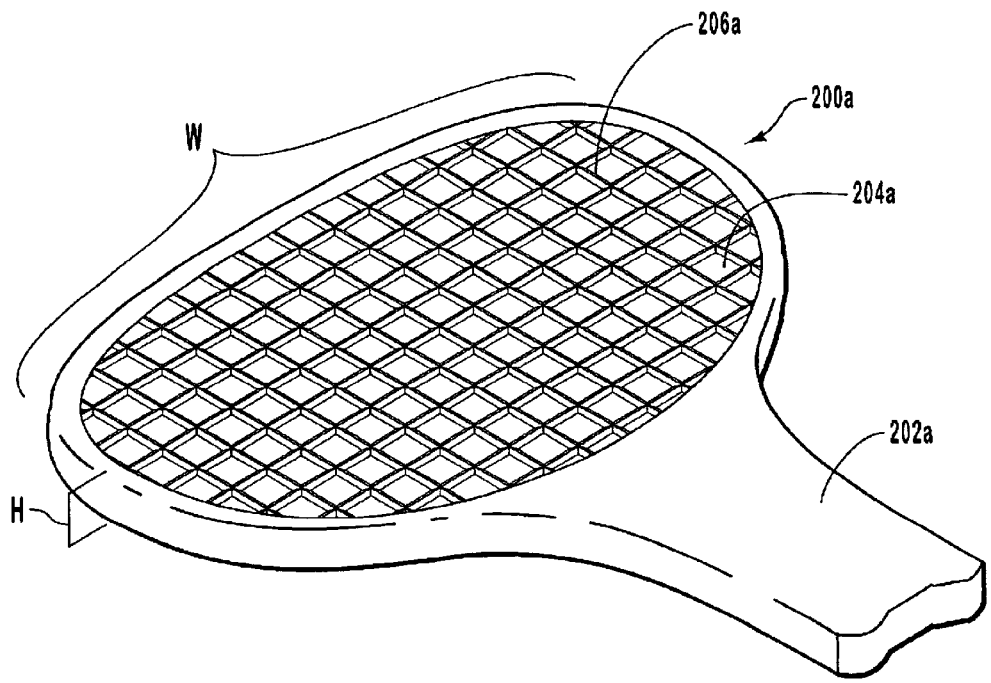
FIG. 13A shows an embodiment of a scraper head of the present invention having triangular shaped crisscrossing ridges thereon (the ridges being preferably perpendicular to each other, as shown) that may be employed for manual or powered tongue scraping. The crisscrossing ridges may be employed to clean the tongue by brushing in a front to back or side to side direction.
Figure 13B:
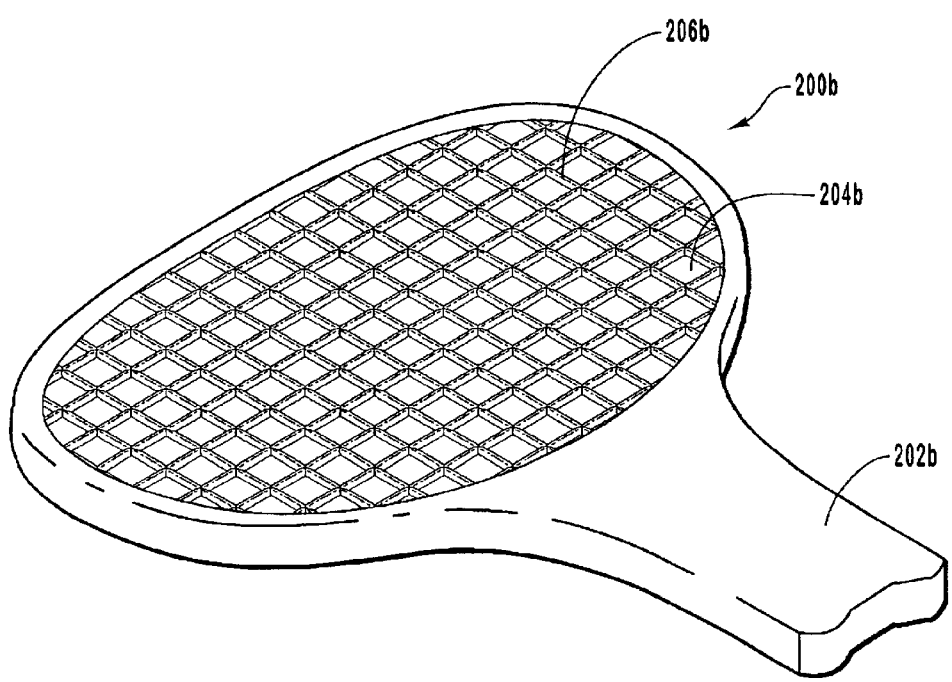
FIG. 13B shows an embodiment of a scraper head of the present invention having crisscrossing rounded ridges thereon (the ridges being preferably perpendicular to each other, as shown) that may be employed for manual or powered tongue scraping.
Figure 13C:
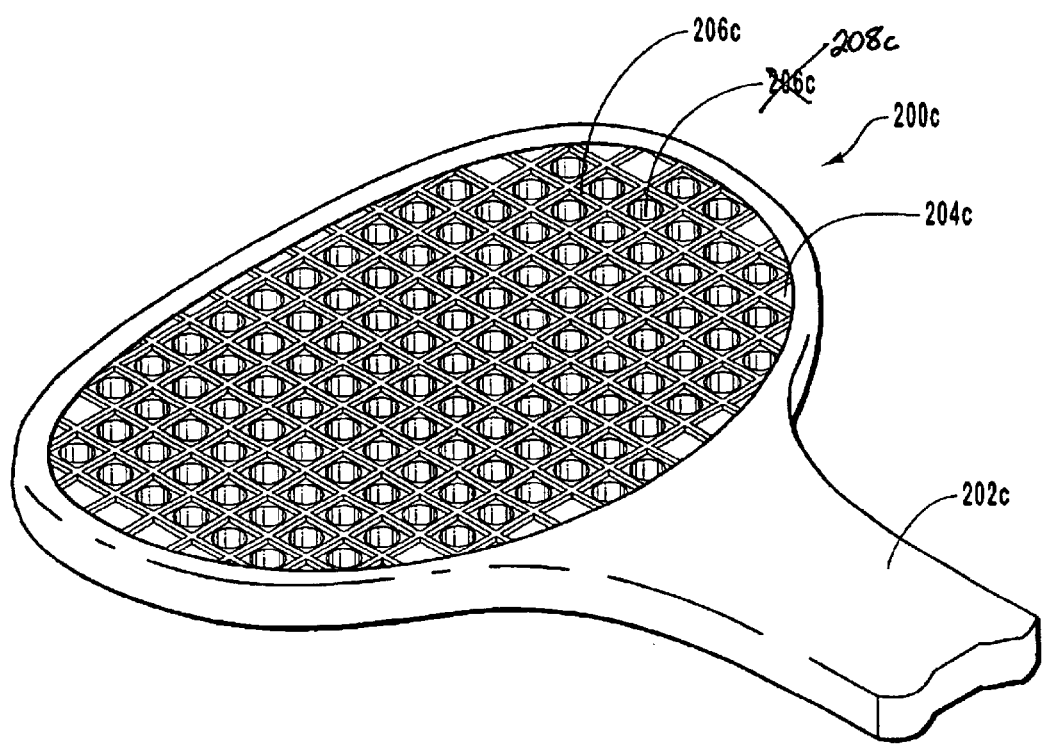
FIG. 13C shows another embodiment of a scraper head of the present invention having crisscrossing ridges thereon (the ridges being preferably perpendicular to each other, as shown) that may be employed for manual or powered tongue scraping and having holes extending through the cleansing head (e.g., from one side to another) to thereby trap particles in the holes as the holes are moved across the tongue.

With reference now to FIGS. 13a–c, another embodiment of a means for cleaning the tongue means is shown. The cleaning means comprises a scraper head 200a–c. Any of scraper heads 200a–c may be coupled to an arm 202a–c that is configured to be coupled a motorized device such as devices 113 or 113a. The scraper head is configured to scrape the tongue.

Scraper heads 200a–c each comprise a respective ridge that can be employed to scrape the tongue, such as a triangular shaped ridge 206a, a rounded ridge 206b, and/or a rectangular shaped ridge 206c. Each of these ridges extend from a cleansing head 204a–c of the respective scraper. Hole 208c; that extend through cleansing head 204c may also be employed, the rims of the holes scraping the surface of the tongue. A mouth cleaning system of the present invention may thus also include a tongue scraping head and arm that is selectively coupled to a motorized moving device such as device 113 or 113a. Thus the powered tongue cleaning device of the present invention may also include a scraper head.

The crisscrossing ridges have a variety of different advantages. The crisscrossing ridges may be employed to clean the tongue by brushing in a front to back or side to side direction. This is an improvement over devices that only scrape in one direction. As shown, the ridges are preferably perpendicular to each other, but are not necessarily perpendicular.

Each of the brush heads disclosed herein is an example of a means for brushing the tongue. The various motorized devices disclosed herein such as motorized devices 113, 113a and all the different variants listed in the discussed above relating thereto are examples of a means for moving the means for brushing tongue. Thus, a variety of motorized devices such as ultrasonic devices, sonic devices, oscillating, spinning and vibrating devices may be employed as the motorized device that moves the brush head of the present invention. These and variety of other means for moving may be employed in order to cause the brush head to vibrate, oscillate or spin, for example.

Figure 9:
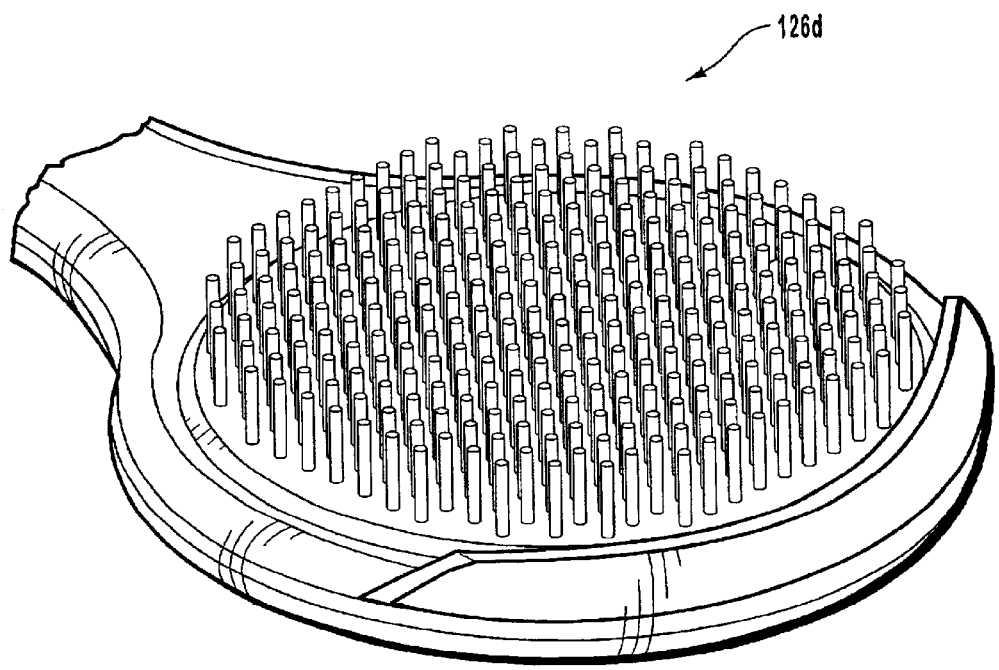
FIG. 9 is a view of another brush head of the present invention that may be employed for manual or powered tongue brushing.
Figure 10:
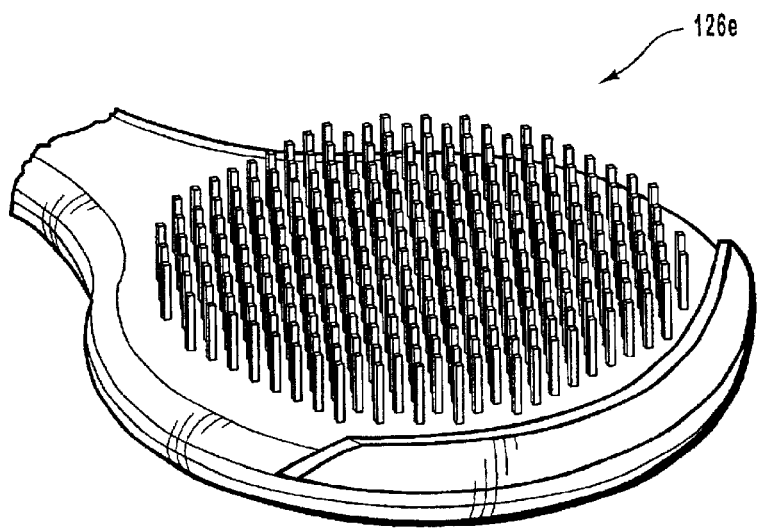
FIG. 10 is a view of another brush head of the present invention that may be employed for manual or powered tongue brushing.
Figure 11A:
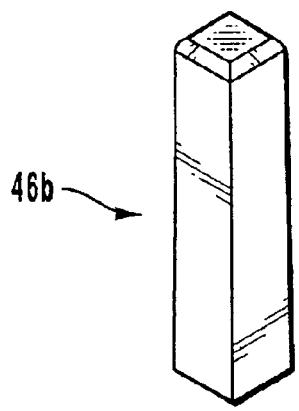
FIGS. 11a–11d are views of alternate bristles of the present invention.
Figure 11B:
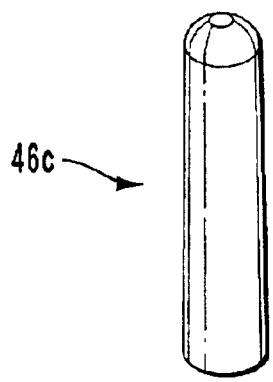
Figure 11C:
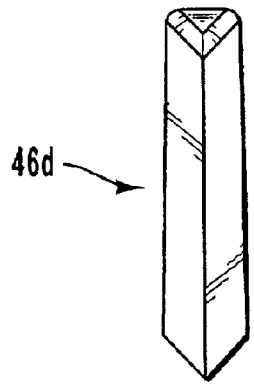
Figure 11D:
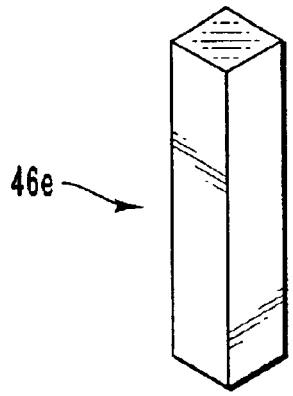
Figure 11E:
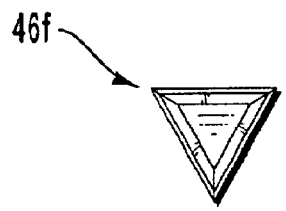
FIGS. 11e–11f are cross sectional views of alternate bristles of the present invention.
Figure 11F:
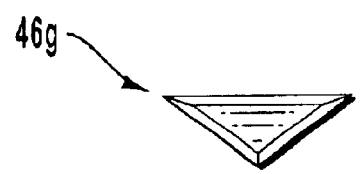
Figure 12A:
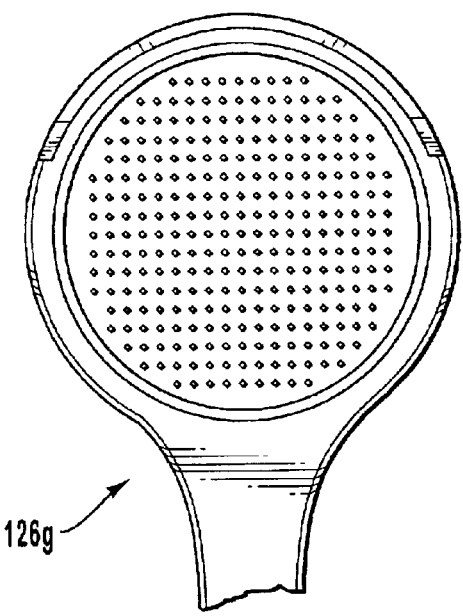
FIGS. 12a–12d are views of brush heads of the present invention having bristle patterns that may be employed for manual or powered tongue brushing.
Figure 12B:
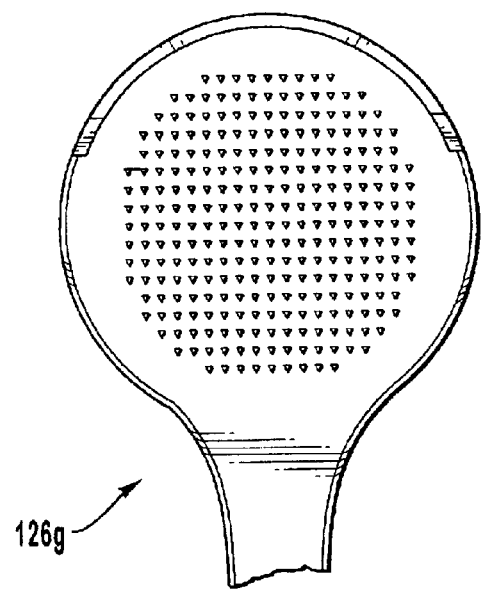
Figure 12C:
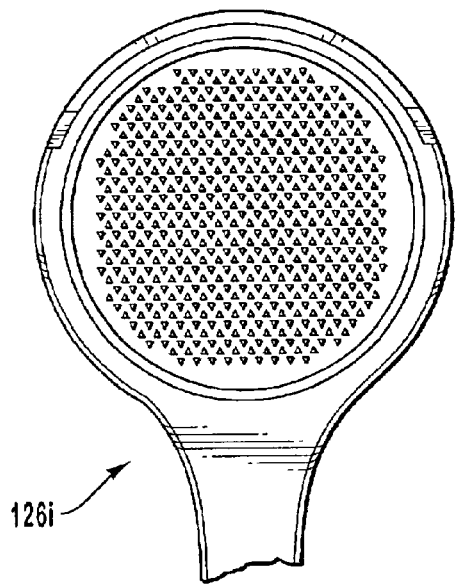
Figure 12D:
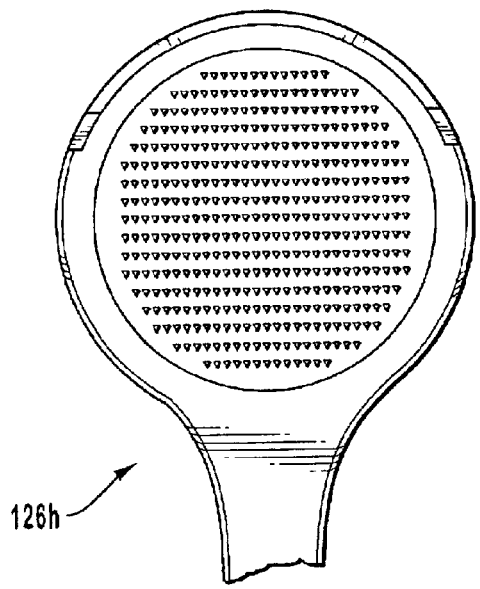

FIGS. 9–10 demonstrate additional examples of brush heads 126d and 126e of the present invention, each of which have different shaped bristles coupled thereto. Thus, the brush head of the present invention may employ a variety of different bristles and additional shaped bristles are shown in FIGS. 11A–D, which show such optional bristles in a perspective view and in FIGS. 11E–F, which show such optional bristles from a top view. FIGS. 12A–12D show optional configurations for the bristles, each of which are merely examples of patterns that can be employed in the present invention.

Although this invention has been described in terms of a certain preferred embodiment, other embodiments apparent to those of ordinary skill in the art are also within the scope of this invention. Accordingly, the scope of the invention is intended to be defined only by the claims that follow.

What is claimed is:

1. A portable, powered, hand-held tongue cleaning device, comprising:
    a brush head configured to brush the tongue, the brush head comprising an essentially flat brush portion having a plurality of flocked fibers randomly adhered to said brush portion; and
    means for moving the brush head such that the brush head moves against the surface of the tongue as the user holds the means for moving the brush head,
    wherein the means for moving is configured so as to enable a user to hold the tongue cleaning device and direct the brush head into the mouth of the user to thereby facilitate a tongue cleaning procedure in the user's mouth; and
    wherein the brush head has a height that is substantially less than the width thereof, such that the configuration of the brush head minimizes the elicitation of a gag reflex when the device is used to clean the tongue.

2. A device as recited in claim 1, wherein the means for moving comprises (i) a housing configured to be grasped by a user; (ii) a motor assembly coupled to the housing; and (iii) an arm coupled to the brush head and the housing.

3. A device as recited in claim 2, wherein the arm is movably coupled to the housing.

4. A device as recited in claim 2, wherein the motor assembly is configured to move the arm.

5. A device as recited in claim 1, wherein the width of the brush head is about 0.5 inch to about 2 inch.

6. A device as recited in claim 5, wherein the height of the brush head is about 0.03 inch to about 0.35 inch.

7. A device as recited in claim 6, wherein the width of the brush head is about 0.75 to about 1.4 inch.

8. A device as recited in claim 7, wherein the height of the brush head is less then about 0.21 inch.

9. A portable, powered, hand-held tongue cleaning device, comprising:
    a brush head comprising an essentially flat brush portion having a plurality of flocked fibers randomly adhered to said brush portion configured to brush the tongue; and a motorized device coupled tho brush head and configured to move the brush head such that the brush head of the moves against the surface of the tongue as the user holds the cleaning device;

wherein the motorized device is configured so as to enable a user to hold the tongue cleaning device and direct the brush head into the mouth of the user to thereby facilitate a tongue cleaning procedure in the user's mouth; and wherein the brush head has a height that is substantially less than the width thereof, such that the configuration of the brush head minimizes the elicitation of a gag reflex when the device is used to clean the tongue.

10. A device as recited in claim 9, wherein the brush head has a generally flat profile.

11. A device as recited in claim 9, wherein the motorized device configured to move the brush head comprises (i) a housing configured to ho grasped by a user; (ii) a motor assembly coupled to the housing; and (iii) an arm coupled to the brush head.

12. A device as recited in claim 11, wherein the arm couples the brush head to the housing and wherein the motor assembly is disposed within the housing, the motor assembly configured to move the arm upon actuation of the motor assembly.

13. A device as recited in claim 9, wherein the device comprises a vibrating device.

14. A portable, powered, hand-held tongue cleaning device, comprising:

a housing configured to enable a user to grasp the tongue cleaning device as the tongue cleaning device is directed by the user to facilitate a tongue cleaning procedure in the user's mouth, said housing having a first end and a second end;

an arm coupled to the housing;

a brush head coupled to the arm, the brush head comprising an essentially flat brush portion having a plurality of flocked fibers randomly adhered to said brush portion and configured to clean tongue surfaces as the brush head is moved against the surface of the tongue; and means disposed within the housing for moving the arm such that the brush head moves against the surface of the tongue as the user holds the housing of the device;

wherein the brush head has a height that is substantially less than the width thereof, such that the configuration of the brush head minimizes the elicitation of a gag reflex when the device is used to clean the tongue.

15. A device as recited in claim 14, wherein the ratio of the height to the width of the brush head is in the range of about 0.015 to about 0.7.

16. A device as recited in claim 14, wherein the ratio of the height to the width of the brush head is in the range of about 0.017 to about 0.46.

17. A device as recited in claim 14, wherein the ratio of the height to the width of the brush head is in the range of about 0.02 to bout 0.35.

18. A device as recited in claim 14, wherein the brush head has a generally flat profile.

19. A device as recited in claim 14, wherein the flocked fibers extend from the brush portion such that the fibers are urged against the tongue as the brush head is pushed downward toward the tongue.

20. A device as recited in claim 19, wherein the flocked fibers are electrostatically coupled to the brush portion.

21. A device as recited in claim 14, wherein the arm is movably coupled to the housing.

22. A device as recited in claim 14, wherein the means for moving the brush head comprises a motor assembly disposed within the housing.

23. A device as recited in claim 22, wherein the motor assembly is configured to vibrate the arm, the motor assembly comprising a motor and a power source coupled to the motor, at least a portion of the power source also being disposed within the housing.

24. A portable, powered, hand-held tongue cleaning device, comprising:

a housing configured to enable a user to grasp the tongue cleaning device as the tongue cleaning device is directed by the user to facilitate a tongue cleaning procedure in the user's mouth, said housing having a first end and a second end;

an arm coupled to the housing;

a brush head coupled to the arm, the brush head comprising an essentially flat brush portion having a plurality of flocked fibers randomly adhered to said brush portion and configured to clean tongue surfaces as the brush head is moved against the surface of the tongue; and a motor assembly configured to move the arm such that the brush head moves against the surface of the tongue as the user holds the housing of the device;

wherein the brush head has a height that is substantially less than the width thereof, such that the configuration of the brush head minimizes the elicitation of a gag reflex when the device is used to clean the tongue.

25. A device as recited in claim 24, wherein the arm is curved, the curved arm enabling the brush to extend far enough to reach one's throat and follow the curvature of the tongue as it extends down into the throat.

26. A device as recited in claim 24, wherein the arm movably couples the brush head to the housing, and wherein the motor assembly is configured to vibrate the arm.

27. A portable, powered, hand-held tongue cleaning device, comprising:

a housing configured to enable a user to grasp the tongue cleaning device as the tongue cleaning device is directed by the user to facilitate a tongue cleaning procedure in the user's mouth said housing having a first end and a second end;

a scraper head con figured to clean tongue surfaces as the scraper head is moved against the surface of the tongue, the scraper head comprising a plurality of ridges that intersect to form a crisscrossing grid pattern; and an arm coupling the scraper head to the housing; and a motor assembly configured to vibrate the arm as the scraper head is moved against the surface of the tongue.

28. A device as recited in claim 27, wherein the scraper head has a height that is no greater than about 0.3 inch, such that the configuration of the scraper head minimizes the elicitation of a gag reflex when the device is used to clean the tongue.

29. A device as recited in claim 27, wherein the scraper head further defines at least one aperture formed through the scraper head.

30. A device as recited in claim 29, wherein the scraper head defines a plurality of apertures, at least two apertures being separated by some of the intersecting ridges.

31. A device as recited in claim 27, wherein the intersecting ridges are substantially perpendicular.

32. A device as recited in claim 27, wherein the ridges comprise triangular shaped ridges.

33. A device as recited in claim 27, wherein the ridges comprise rectangular shaped ridges.

34. A device as recited in claim 27, wherein the ridges comprise round shaped ridges.

35. A portable, powered, hand-held system for cleaning the mouth, the system comprising:
- a brush head comprising an essentially flat brush portion having a plurality or flocked fibers randomly adhered to said brush portion configured to clean the tongue;
- a toothbrush head configured to clean the teeth; and
- a motorized device configured to be selectively coupled to at least one of the brush head and the toothbrush head, the motorized device configured to move the at least one head that is coupled thereto such that the at least one head moves against the desired surface as the user holds the cleaning device;
- wherein the motorized device is configured so as to enable a user to hold the tongue cleaning device and direct the at least one head into the mouth of the user to thereby facilitate a tongue cleaning procedure in the user's mouth.

36. A system as recited in claim 35, wherein comprising a scraper head.

37. A system as recited in claim 36, wherein the scraper head permits cleaning in a front to back or side to side motion.

38. A system as recited in claim 37, wherein the scraper head comprises ridges forming a crisscrossing pattern, such that the scraper head can clean in both side to side and front to back motions.

* * * * *